(12) United States Patent
Schneider et al.

(10) Patent No.: US 6,613,306 B1
(45) Date of Patent: *Sep. 2, 2003

(54) ULTRASOUND CONTRAST AGENTS AND METHODS OF MAKING AND USING THEM

(75) Inventors: Michel Schneider, Troinex (CH); Feng Yan, Carouge (CH); Pascal Grenier, deceased, late of Ambilly (FR), by Nadine Garcel, legal representative; Jerome Puginier, Le Chable-Beaumont (FR); Marie-Bernadette Barrau, Genéve (CH); Philippe Bussat, Feigeres (FR); Eva Hybl, Heidelberg (DE); Daniel Bichon, Montpellier (FR)

(73) Assignee: Bracco International B.V., Amsterdam (NL)

( * ) Notice: Subject to any disclaimer, the term of this patent is extended or adjusted under 35 U.S.C. 154(b) by 0 days.

This patent is subject to a terminal disclaimer.

(21) Appl. No.: 09/401,838

(22) Filed: Sep. 22, 1999

Related U.S. Application Data

(63) Continuation-in-part of application No. 08/910,152, filed on Aug. 13, 1997, now Pat. No. 6,200,548, which is a division of application No. 08/288,550, filed on Aug. 10, 1994, now Pat. No. 5,711,933, which is a division of application No. 08/033,435, filed on Mar. 18, 1993, now abandoned, which is a division of application No. 07/695,343, filed on May 3, 1991, now abandoned, application No. 09/401,838, which is a continuation-in-part of application No. 08/853,936, filed on May 9, 1997, now Pat. No. 6,110,443, which is a division of application No. 08/456,385, filed on Jun. 1, 1995, now Pat. No. 5,658,551, which is a division of application No. 08/315,347, filed on Sep. 30, 1994, now Pat. No. 5,531,980, which is a division of application No. 08/128,540, filed on Sep. 29, 1993, now Pat. No. 5,380,519, which is a division of application No. 07/775,989, filed as application No. PCT/EP91/00620 on Apr. 2, 1991, now Pat. No. 5,271,928, application No. 09/401,838, which is a continuation-in-part of application No. 08/740,653, filed on Oct. 31, 1996, which is a division of application No. 08/380,588, filed on Jan. 30, 1995, now Pat. No. 5,578,292, which is a division of application No. 07/991,237, filed on Dec. 16, 1992, now Pat. No. 5,413,774, application No. 09/401,838, which is a continuation-in-part of application No. 08/637,346, filed on Apr. 25, 1996, which is a division of application No. 08/352,108, filed on Nov. 30, 1994, now Pat. No. 5,556,610, which is a continuation-in-part of application No. 07/991,237, which is a division of application No. 07/991,237, filed on Dec. 16, 1992, now Pat. No. 5,413,774, application No. 09/401,838, which is a continuation-in-part of application No. 08/637,346, filed on Apr. 25, 1996, which is a division of application No. 08/352,108, filed on Nov. 30, 1994, now Pat. No. 5,556,610, which is a continuation-in-part of application No. 07/991,237.

(30) Foreign Application Priority Data

| Apr. 2, 1990 | (EP) | 90810262 |
|---|---|---|
| Apr. 2, 1991 | (EP) | PCT/EP91/00620 |
| Jan. 24, 1992 | (EP) | 92810046 |
| Dec. 15, 1993 | (EP) | 93810885 |

(51) Int. Cl.$^7$ .................................................. A61B 8/00
(52) U.S. Cl. .................................... 424/9.52; 424/9.51
(58) Field of Search .......................... 424/9.51, 9.52, 424/450; 600/431, 458

(56) References Cited

U.S. PATENT DOCUMENTS

| 3,650,831 A | 10/1971 | Jungermann |
|---|---|---|
| 3,615,972 A | 2/1972 | Dow |
| 3,900,420 A | 8/1975 | Sebba |
| 3,968,203 A | 7/1976 | Spitzer et al. |
| 4,027,007 A | 5/1977 | Messina |
| 4,192,859 A | 3/1980 | Mackaness et al. |
| 4,224,179 A | 9/1980 | Schneider |
| 4,229,360 A | 10/1980 | Schneider |
| 4,235,871 A | 11/1980 | Papahadjopoulos et al. |
| 4,265,251 A * | 5/1981 | Tickner .................. 128/662.01 |
| 4,276,885 A * | 7/1981 | Tickner et al. ......... 128/662.01 |
| 4,316,391 A | 2/1982 | Tickner |
| 4,370,349 A | 1/1983 | Evans |
| 4,442,843 A | 4/1984 | Rasor |
| 4,466,442 A | 8/1984 | Hilmann et al. |
| 4,544,545 A | 10/1985 | Ryan |

(List continued on next page.)

FOREIGN PATENT DOCUMENTS

| CA | 1232837 | 2/1988 |
|---|---|---|
| CA | 1239092 | 7/1988 |
| CA | 2077383 | 3/1993 |
| DE | A 41 27 442 | 2/1993 |
| EP | A 131 540 | 1/1985 |
| EP | A 324 938 | 7/1989 |
| EP | 359 246 A3 | 3/1990 |
| EP | 359 246 A2 | 3/1990 |
| EP | A 458 745 | 11/1991 |
| EP | A 554 213 | 4/1993 |
| GB | 1044680 | 10/1966 |
| GB | 213 5647 | 9/1984 |
| NZ | 253115 | 1/1996 |
| WO | WO-A-80/2365 | 11/1980 |

(List continued on next page.)

OTHER PUBLICATIONS

Swanson, Pharmaceuticals in Medical Imaging; MacMillan Publishing, NY pp 682–687 (1990).*

(List continued on next page.)

Primary Examiner—Michael G. Hartley
(74) Attorney, Agent, or Firm—Nixon & Vanderhye P.C.

(57) ABSTRACT

Gas or air filled microbubble suspensions in aqueous phases usable as imaging contrast agents in ultrasonic echography. They contain surfactants and, optionally, hydrophilic stabilizers. The surfactants can be in the form of liposomes. The suspensions are obtained by exposing the surfactants to air or a gas before or after admixing with an aqueous phase. One can impart outstanding resistance against collapse under pressure to these gas-filled microbubbles used as contrast agents in ultrasonic echography by using as fillers gases whose solubility in water, expressed in liter of gas by liter of water under standard conditions, divided by the square root of the molecular weight does not exceed 0.003. Contrast agents with particular mixtures of gases are also disclosed that have advantageous properties.

5 Claims, 7 Drawing Sheets

U.S. PATENT DOCUMENTS

| | | | |
|---|---|---|---|
| 4,572,203 A | 2/1986 | Feinstein | |
| 4,657,756 A | 4/1987 | Rasor | |
| 4,681,119 A | 7/1987 | Rasor | |
| 4,684,479 A | 8/1987 | D'Arrigo | |
| 4,718,433 A | 1/1988 | Feinstein | |
| 4,774,958 A | * 10/1988 | Feinstein | 424/9.52 |
| 4,832,941 A | 5/1989 | Berwing | |
| 4,844,882 A | * 7/1989 | Widder et al. | 424/9.52 |
| 4,859,363 A | 8/1989 | Davis et al. | |
| 4,900,540 A | 2/1990 | Ryan et al. | |
| 4,927,623 A | 5/1990 | Long | |
| 4,957,656 A | 9/1990 | Cerny | |
| 5,049,322 A | 9/1991 | Devissaguet et al. | |
| 5,088,499 A | 2/1992 | Unger | |
| 5,089,181 A | 2/1992 | Hauser | |
| 5,123,414 A | 6/1992 | Unger | |
| 5,137,928 A | 8/1992 | Erbel | |
| 5,141,738 A | 8/1992 | Rasor | |
| 5,147,631 A | * 9/1992 | Glajch et al. | 424/9.52 |
| 5,149,319 A | 9/1992 | Unger | |
| 5,190,982 A | 3/1993 | Erbel | |
| 5,195,520 A | 3/1993 | Schlief | |
| 5,205,287 A | 4/1993 | Erbel | |
| 5,209,720 A | 5/1993 | Unger | |
| 5,271,928 A | 12/1993 | Schneider | |
| 5,283,067 A | 2/1994 | Geller et al. | |
| 5,312,615 A | * 5/1994 | Schneider et al. | 424/5 |
| 5,352,436 A | 10/1994 | Wheatley | |
| 5,364,612 A | 11/1994 | Goldenberg | |
| 5,380,411 A | 1/1995 | Schlief | |
| 5,380,519 A | 1/1995 | Schneider | |
| 5,393,524 A | 2/1995 | Quay | |
| 5,409,688 A | 4/1995 | Quay | |
| 5,413,774 A | 5/1995 | Schneider | |
| 5,425,366 A | 6/1995 | Reinhardt | |
| 5,445,813 A | 8/1995 | Schneider | |
| 5,501,863 A | * 3/1996 | Rössling et al. | 424/9.52 |
| 5,531,980 A | 7/1996 | Schneider | |
| 5,536,489 A | 7/1996 | Lohrmann | |
| 5,536,490 A | 7/1996 | Klaveness | |
| 5,552,133 A | 9/1996 | Lambert et al. | |
| 5,556,610 A | 9/1996 | Yan et al. | |
| 5,558,856 A | 9/1996 | Klaveness et al. | |
| 5,567,413 A | 10/1996 | Klaveness | |
| 5,567,414 A | 10/1996 | Schneider | |
| 5,593,687 A | 1/1997 | Rössling et al. | |
| 5,599,523 A | 2/1997 | Beller | |
| 5,601,085 A | 2/1997 | Østensen et al. | |
| 5,639,443 A | 6/1997 | Schutt et al. | |
| 5,643,553 A | 7/1997 | Schneider | |
| 5,658,551 A | 8/1997 | Schneider | |
| 5,669,443 A | * 9/1997 | Budde et al. | 424/9.52 |
| 5,711,933 A | 1/1998 | Bichon et al. | |
| 5,716,597 A | 2/1998 | Lohrmann et al. | |
| 5,730,954 A | * 3/1998 | Albayrak et al. | 424/9.52 |
| 5,776,429 A | 7/1998 | Unger et al. | |
| 5,874,062 A | * 2/1999 | Unger | 424/9.4 |

FOREIGN PATENT DOCUMENTS

| | | | |
|---|---|---|---|
| WO | WO 84/02838 | 8/1984 | |
| WO | WO-A-85-02772 | 7/1985 | |
| WO | WO 88/7365 | 10/1988 | |
| WO | WO 88/09165 | * 12/1988 | A61K/49/04 |
| WO | WO 89/05160 | 6/1989 | |
| WO | WO 91/09629 | 7/1991 | |
| WO | 90/12823 | * 9/1991 | |
| WO | 91/12823 | * 9/1991 | |
| WO | WO 91/12823 | 9/1991 | |
| WO | WO 91/15244 | 10/1991 | |
| WO | WO 92/05806 | 4/1992 | |
| WO | WO A 92/17212 | 10/1992 | |
| WO | WO 92/17213 | 10/1992 | |
| WO | WO 92/17514 | 10/1992 | |
| WO | WO 92/18164 | 10/1992 | |
| WO | WO 92/19273 | 11/1992 | |
| WO | WO 92/21382 | 12/1992 | |
| WO | WO 92/22247 | 12/1992 | |
| WO | 93/02712 | * 2/1993 | |
| WO | WO 93/5819 | 4/1993 | |
| WO | WO 93/06869 | 4/1993 | |
| WO | WO 94/16739 | 8/1994 | |
| ZA | 910961 | 11/1991 | |

OTHER PUBLICATIONS

Nomura, Y et al., Japn. J. Med. Ultrasonics, 18(5):28–34 (1991).*

Lincoff et al., Arch. Opthamology 98:1610–1611 (1980).*

Lincoff et al., Arch. Opthamology 98:1646 (1980).*

Jacobs, Current Eye Research, 5(8):575–578 (1966).*

Gardner et al., Arch Opthalmol. 106:1188–1189 (1988).*

Dupont Technical Bulletin (El Dupont De Nemours, Wilmington, DE) pp 1–10 (1987).*

Biochemistry/Ed. Stryer—2 Ed., San Francisco, Freeman, pp. 208–209 (1981).

Concise Encyclopedia Of Polymer Sci. and Engin., Wiley, pp. 12–13 (1990).

Encyclopedia of Polymer Science and Engineering, 2nd ed., 10, p. 95, Wiley & Sons, 1987).

Encyclopedia of Polymer Science and Engineering, pp. 164–169, Wiley & Sons, 1985.

""Freon" Fluorocarbons Properties and Applications," *Dupont Technical Bulletin*, pp. 1–11 (1964).

"Freon" *DuPont Technical Bulletin*, pp. 1–10 (1987).

Gas Encyclopedia, Elsevier Publishier (1976), CC1F3.

Handbook of Pharmaceutical Excipients: Am. Pharm. Ass. 181–183 (1986).

"Lecithin" in Rompp Chemie Kexikon, p. 2474 (1989–92).

"Lecithin" in Blakiston's Gould Medical Dictionary, 4th Ed., N.Y., Mcgraw–Hill,, p. 749 (1979).

"Lecithin" in Dorland's Illustrated Medical Dictionary, 26 Ed., Philadelphia, Saunders, p. 721 (1981).

Remington's Pharmaceutical Sciences: Mack Publ. Comp., 295–298: 736; 1242–44 (1975).

Barnhart et al., *Invest. Radiol*, 25, 162–164 (1990) "Characterics fo Albunex".

Benita et al., *Journal of Pharmaceutical Science*, 73, pp. 1721–1724 (1984) "Characterization of Drug Loaded Polydilactide Microspheres".

Bleeker, et al., *J. Acoust. Soc. Am.*, 87 (4), Apr. 1990, pp. 1792–1797, "Ultrasonic characterization of Albunex® . . . ".

Bleeker, et al., 1990 *J. Ultrasound Med.*, 9:461–471, (1999), "On the Application of Ultrasonic Contrast Agents . . . ".

Bommer et al., Abstract of the 54 Scient. Sessions, Circulations 64, —203, Abst. 770 (1981).

Crommelin et al., Pharm. Res., pp. 159–163 (1984) "Stability of Liposomes on Storage . . . ".

Crommelin et al., Liposomes as Drugs Carriers Symp., pp. 88–93 (1986) "Freezing and Freeze Drying of Liposomes".

de Gruyter, "Phospholipids", *Concise Encyclopedia of Biochemistry*, Berlin, pp. 348–349 (1983).

deJong, et al., *Ultrasonics*, 1992, vol. 30, No. 2, pp. 95–103, "Absorption and scatter of encapsulated gas filled microspheres . . . ".

deJong, et al., *Ultrasonics*, 1991, vol. 29 Jul., pp. 324–330, "Principles and recent developments in ultrasound".

Edwards, et al. *J. Acoust. Soc. Am.*, vol. 70, No. 3 (1983), "Scattering of focused ultrasound by spherical microparticles".

Epstein, et al., *J. Chem. Physics*, vol. 18, No. 11, pp. 1505–1509, Nov. 1950, "On the Stability of Gas Bubbles in Liquid–Gas Solutions".

Feinstein, et al., *JACC*, vol. 16, No. 2, 8/90:316–24, "Safety and Efficacy of a New Transpulmonary Ultrasound Agent . . . ", *Amer. Hearts Assn. Monograph Circulation*, Part II, vol. 72, No. 4, Oct. 1985, *Abstracts of the 58$^{th}$Scientific Ses.*

Feinstein, et al., *Am. J. of Physiologic Imaging*, 1:12–18 (1986), "Myocardial Contrast Echocardiography . . . ".

Feinstein, *J. of the Amer. Coll. of Cardiol*, 8:251–253 (1986) "Myocardial Perfusion Imaging . . . ".

H. Fessi, et al., "Nanocapsule formation by interfacial polymer deposition . . . ," *Int. J. Pharm.*, 1989, vol. 55, No. 1, pp. R1–R4.

Fieser and Fieser, *Organic Chemistry*, 3rd ed. (1956) p. 847.

Fobbe, et al., *Furtschr Rontgenstr*, 154.3 (1991) 242–245, "Farbkodierte Duplexsonographic und Ultraschallkontrast mittel . . . ".

Ganguly et al., "Structure of hollow polystyrene microspheres . . . " *J. Microencapsulation*, vol. 6, No. 2, 193–198 (1989).

Gardner, et al., (1988), "A Survey of Intraocular Gas Use in North America," *Arch. Ophthalmol.*, 106:1188–1189.

Goldberg et al., *Radiology*, 177, pp. 713–717 (1990) "Hepatic Tumors . . . ".

Helzel, *Fortschr. Rontgenste*, 140, pp. 337–340 (1984) "Erste Erfahrurgen . . . ".

Henry–Michelland et al., *Colloids and Surfaces*, 14, pp. 269–276 (1985) "Lyophilization and Rehydration of Liposomes".

Jacobs, "Intraocular gas measurement using A–scan ultrasound," *Current Eye Research*, vol. 5, No. 8, 1986, pp. 575–578.

Keller et al, *Circulation Res*, 65, 458–467 (1989) "The Behavior of Sonicated Albumin . . . ".

Krause et al., *International Journal of Pharmaceutics.*, 27, pp. 145–155 (1985) "Polylactic acid nanoparticle . . . ".

Levene et al, *J. Acoust. Soc. Am.*, 87 (Suppl) 69 (1990) "Characterization of Albunex . . . ".

Lincoff, et al., Intravitreal Longevity of Three Perfluorocarbon Cases, *Arch. Ophthalmology*, 98:1610–1611 (1980).

Lincoff, et al., "Intravitreal Expansion of Perfluorocarbon Bubbles," *Arch. Ophthalmology*, 98:1646 (1980).

Lincoff, et al., "The Perfluorocarbon Gases in the Treatment of Retinal Detachment,"*Ophthalmology*, 90(5):546–551 (1983).

Lincoff, et al., "Perfluoro–n–butane: A Gas for Maximum Duration Retinal Tamponade," *Arch. Ophthalmology*, 101:460–463 (1983).

K. Makino, "Preparation and in vivo degradation properties . . . ," *Chem. Pharm. Bull.*, (1985), vol. 33, No. 3, pp. 1195–1201.

Mattrey et al., *Radiology*, 148, pp. 759–762 (Dec. 1982) "UHM Sound; Perfluoroctylbr omide . . . ".

*Chem Abs.*, vol. 102. No. 3, 21 (Jan. 1985), Maynard et al., "Ultrasonic absorption by liposomes".

Meltzer, et al., *Ultrasound in Med. & Biol.*, vol. 7, No. 4, pp. 377–384, 1981, "Transmission of Ultrasonic Contrast Through the Lungs".

Miller et al., *J. Amer. Soc. Anesthesiol.*, 36 339–351 (1971) "Physicochemical Approaches . . . ".

Möhwald, *Annu. Rev. Phys. Chem.*, 441–76 (1990) "Phospholipid and Phospholipid–Protein Monolayers At The Air/Water Interface".

Murrell et al, "Properties of liquids and solutions", Wiley, p. 276 (1982).

Nomura, et al., "US Contrast Enhancement of Hepatic Tumor with Helium Gas Microbubbles: A Preliminary Report," *Jpn. J. Med. Ultrasonics*, vol. 18, No. 5, 1991, pp. 444–450.

O'Hara et al, *Journal of Membrane Science*, 23 (1985) 1–9, "Preparation of ethylcellulose . . . ".

Ohta, et al., *Jpn. J. Med. Ultrasonics*, vol. 18, No. 4 (1991), "Effect of the Contrast Agent and the Agitation Met."

Ophir, et al., *Ultrasound in Med. & Biol.*, vol. 15, No. 4, pp. 319–333, 1989, "Contrast Agents in Diagnostic Ultras."

Ostro in *Spektrum d. Wiss*, 94–95, 98 (Mar. 1987). "Liposomen . . . ".

Özer et al., *Acta Pharm. Tech.* 34, pp. 129–139 (1988) "Influence of Freezing and Freeze Drying on Stability of Liposome . . . ".

Park, et al., *Journal of Chemical And Engineering Data*, vol. 27, No. 3 (1982), "Solubility of Gases in Liquids. 14. Bunsen Coefficients for Several Fluorine–Containing Gases (Freons) Dissolved in Water at 298.15K".

Peters et al., *Am. J. Ophthalmol.* 100 pp. 831–839 (1985) "The non expansive, equilibrated concentration of perfuoropropane in the eye".

Puisieux et al., *Bull. Soc. Pharm. Bordeaux*, 123, pp. 111–126 (1984) "Les Liposomes . . . ".

Rompp Lex. Chemie. 8 Aufl. Stuttgart: Franckh; Bd. Z: Cm–G, (1981): Bd 3; H–L, (1983); Bd 4, M–Pk (1985) "Porositat".

Schlief, *Current Opinion in Radiology*, 1993, 3:198–207, "Ultrasound Contrast Agents".

Schneider, et al., Investigative Radiol., 26(1), pp. S190–S191 (1991) "A New Ultrasound Contrast Agent Based on Biodegradable Polymers Microballoon".

Schneider, et al., Investigative Radiol., 29(2), pp. S149–51 (1991) "The Use of Polymers Microballoons as Ultrasound Contrast Agent . . . ".

Swanson, pp. 682–687, "Chapter 22: Enhancement Agents for Ultrasound: Fundamentals," *Pharmaceuticals In Medical Imaging*, (1990).

Szoka et al, *PNAS* 75, pp. 4194–4198 (Sep. 1978) "Procedure for preparation of Liposomes . . . ".

Tomlinson, *Int. J. Pharm. Tech. & Prod. Mfr.*, 4, pp. 49–57 (1983) "Microsphere Delivery Systems . . . ".

Ulmius et al, Biochem., 21, p. 1553 (1982) "Molecular organization . . . ".

K. Uno, et al., "A new method of preparing monocored . . . ," *J. Microencapsulation*, 1984, vol. 1, No. 1, pp. 3–8.

Violante, et al., *Investigative Radiology*, vol. 26, Nov. Supp 1991, "Particle–Stabilized Bubbles for Enhanced Organ Ultrasound Imaging".

Voigt et al., "Lzithine" in Lehrb. d. pharm. Tech. i, uberarb. Aufl.—Weinheim; VCH, p. 367 (1979).

Wheatley et al, Biomaterials 11, pp. 713–717 (1990) "Contrast agents for diagnostic ultrasound . . . ".

Widder, et al. *AJR*:147, Aug. 1986, "Microbubbles as Contrast Agent for Neurosonography and Ultrasound . . . ".

Zhang, et al., *J. East China Inst. Chem. Tech.*, 12(3) 343–345 (1986) "A Study on the Solubilities of F22 and C2F4 in Aqueous Solutions of HCl and NaCl".

Zeghlouol et al, *Journal de Chimie Physique*, 83; 665–671 (1986) "NMR And Microcalorimetry Study Of The Solubility Of Certain Halons And Their Interactions with Human Serum Albumin".

* cited by examiner

ULTRASOUND CONTRAST AGENTS AND METHODS OF MAKING AND USING THEM

This application is a continuation-in-part of Ser. No. 08/910,152, filed Aug. 13, 1997, U.S. Pat. No. 6,200,548, which is a divisional of Ser. No. 08/288,550, filed Aug. 10, 1994, now U.S. Pat. No. 5,711,933, which is a divisional of Ser. No. 08/033,435, filed Mar. 18, 1993 now abandoned, which is a divisional of Ser. No. 07/695,343, filed May 3, 1991 now abandoned, which originated from EP 90810367.4, filed May 18, 1990. This application is also a continuation-in-part of Ser. No. 08/853,936, filed May 9, 1997, U.S. Pat. No. 6,110,443 which is a divisional of Ser. No. 08/456,385, filed Jun. 1, 1995, now U.S. Pat. No. 5,658,551, which is a divisional of Ser. No. 08/315,347, filed Sep. 30, 1994, now U.S. Pat. No. 5,531,980, which is a divisional of Ser. No. 08/128,540, filed Sep. 29, 1993, now U.S. Pat. No. 5,380,519, which is a divisional of Ser. No. 07/775,989, filed Nov. 20, 1991, now U.S. Pat. No. 5,271,928, which originated from and is a 371 of PCT/EP91/00620, filed Apr. 2, 1991, and EP 90810262.7, filed Apr. 2, 1990. This application is also a continuation-in-part of Ser. No. 08/740,653, filed Oct. 31, 1996, which is still pending, which is a divisional of Ser. No. 08/380,588, filed Jan. 30, 1995, now U.S. Pat. No. 5,578,292, which is a divisional of Ser. No. 07/991,237, filed Dec. 16, 1992, now U.S. Pat. No. 5,413,774, which originated from EP 92810046.0, filed Jan. 24, 1992. This application is also a continuation-in-part of Ser. No. 08/637,346, filed Apr. 25, 1996, which is a divisional of Ser. No. 08/352,108, filed Nov. 30, 1994, now U.S. Pat. No. 5,556,610, which originated from EP 93810885.9, filed Dec. 15, 1993 and which is a continuation-in-part of Ser. No. 07/991,237. All of the aforementioned applications are hereby incorporated by reference herein in their entirety.

SUMMARY

The present invention concerns media adapted for injection into living bodies, e.g., for the purpose of ultrasonic echography and, more particularly, injectable liquid compositions comprising microbubbles of air or physiologically acceptable gases as stable dispersions or suspensions in an aqueous liquid carrier. These compositions are mostly usable as contrast agents in ultrasonic echography to image the inside of blood-stream vessels and other cavities of living beings, e.g., human patients and animals. Other uses however are also contemplated as disclosed hereafter.

The invention also comprises dry compositions which, upon admixing with an aqueous carrier liquid, will generate the foregoing sterile suspension of microbubbles thereafter usable as contrast agents for ultrasonic echography and other purposes. The present invention also concerns stable dispersions or compositions of gas filled microvesicles in aqueous carrier liquids. These dispersions are generally usable for most kinds of applications requiring gases homogeneously dispersed in liquids. One notable application for such dispersions is to be injected into living beings, for instance for ultrasonic echography and other medical applications. The invention also concerns the methods for making the foregoing compositions including some materials involved in the preparations, for instance pressure-resistant gas-filled microbubbles, microcapsules and microballoons.

BACKGROUND

It is well known that microbodies of air or a gas (defined here as microvesicles), e.g., microbubbles or microballoons, suspended in a liquid are exceptionally efficient ultrasound reflectors for echography. In this disclosure, the term "microbubble" specifically designates air or gas globules in suspension in a liquid which generally results from the introduction therein of air or a gas in divided form, the liquid preferably also containing surfactants or tensides to control the surface properties thereof and the stability of the bubbles. More specifically, one may consider that the internal volume of the microbubbles is limited by the gas/liquid interface, or in other words, the microbubbles are only bounded by a rather evanescent envelope involving the molecules of the liquid and surfactant loosely bound at the gas to liquid junction boundary.

The term "microcapsule" or "microballoon" designates preferably air or gas bodies with a material boundary or envelope formed of molecules other than that of the liquid of suspension, e.g., a polymer membrane wall. Both microbubbles and microballoons are useful as ultrasonic contrast agents. For instance, injecting into the blood-stream of living bodies suspensions of gas microbubbles or microballoons (in the range of 0.5 to 10 $\mu$m) in a carrier liquid will strongly reinforce ultrasonic echography imaging, thus aiding in the visualization of internal organs. Imaging of vessels and internal organs can strongly help in medical diagnosis, for instance for the detection of cardio-vascular and other diseases.

The formation of suspensions of microbubbles in an injectable liquid carrier suitable for echography can follow various routes, such as by the release of a gas dissolved under pressure in this liquid, or by a chemical reaction generating gaseous products, or by admixing with the liquid soluble or insoluble solids containing air or gas trapped or adsorbed therein. For instance in DE-A-3529195 (Max-Planck Gesell.), there is disclosed a technique for generating 0.5–50 $\mu$m bubbles in which an aqueous emulsified mixture containing a water soluble polymer, an oil and mineral salts is forced back and forth, together with a small amount of air, from one syringe into another through a small opening. Here, mechanical forces are responsible for the formation of bubbles in the liquid.

M. W. Keller et al. (J. Ultrasound Med. 5 (1986), 439-8) have reported subjecting to ultrasonic cavitation under atmospheric pressure solutions containing high concentrations of solutes such as dextrose, Renografin-76, Iopamidol (an X-ray contrast agent), and the like. There the air is driven into the solution by the energy of cavitation.

Other techniques rely on the shaking of a carrier liquid in which air containing microparticles have been incorporated, said carrier liquid usually containing, as stabilizers, viscosity enhancing agents, e.g. water soluble polypeptides or carbohydrates and/or surfactants. It is effectively admitted that the stability of the microbubbles against decay or escape to the atmosphere is controlled by the viscosity and surface properties of the carrier liquid. The air or gas in the microparticles can consist of inter-particle or intra-crystalline entrapped gas, as well as surface adsorbed gas, or gas produced by reactions with the carrier liquid, usually aqueous. All this is fully described for instance in EP-A-0052575 (Ultra Med. Inc.) in which there are used aggregates of 1–50 $\mu$m particles of carbohydrates (e.g., galactose, maltose, sorbitol, gluconic acid, sucrose, glucose and the like) in aqueous solutions of glycols or polyglycols, or other water soluble polymers.

Also, in EP-A-0123235 and EP-A-0122624 (Schering. see also EP-A-0320433) use is made of air trapped in solids. For instance, EP-A-0122624 claims a liquid carrier contrast composition for ultrasonic echography containing microparticles of a solid surfactant, the latter being optionally combined with microparticles of a non-surfactant. As explained in this latter document, the formation of air bubbles in the solution results from the release of the air adsorbed on the surface of the particles, or trapped within the particle lattice, or caught between individual particles, this being so when the particles are agitated with the liquid carrier.

EP-A-0131540 (Schering) also discloses the preparation of microbubbles suspensions in which a stabilized injectable carrier liquid, e.g., a physiological aqueous solution of salt, or a solution of a sugar like maltose, dextrose, lactose or galactose, without viscosity enhancer, is mixed with microparticles (in the 0.1 to 1 $\mu$m range) of the same sugars containing entrapped air. In order that the suspension of bubbles can develop within the liquid carrier, the foregoing documents recommend that both liquid and solid components be violently agitated together under sterile conditions; the agitation of both components together is performed for a few seconds and, once made, the suspension must then be used immediately, i.e., it should be injected within 5–10 minutes for echographic measurements; this indicates that the bubbles in the suspensions are not longlived and one practical problem with the use of microbubbles suspensions for injection is lack of stability with time. The present invention fully remedies this drawback.

In an attempt to cure the evanescence problem, microballoons, i.e., microvesicles with a material wall, have been developed. As said before, while the microbubbles only have an immaterial or evanescent envelope, i.e., they are only surrounded by a wall of liquid whose surface tension is being modified by the presence of a surfactant, the microballoons or microcapsules have a tangible envelope made of substantive material, e.g., a polymeric membrane with definite mechanical strength. In other terms, they are microvesicles of material in which the air or gas is more or less tightly encapsulated.

In U.S. Pat. No. 4,466,442 (Schering), there is disclosed a series of different techniques for producing suspensions of gas microbubbles in a liquid carrier liquid carrier using (a) a solution of a tenside (surfactant) in a carrier liquid (aqueous) and (b) a solution of a viscosity enhancer as stabilizer. For generating the bubbles, the techniques used there include forcing at high velocity a mixture of (a), (b) and air through a small aperture; or injecting (a) into (b) shortly before use together with a physiologically acceptable gas; or adding an acid to (a) and a carbonate to (b), both components being mixed together just before use and the acid reacting with the carbonate to generate $CO_2$ bubbles; or adding an over-pressurized gas to a mixture of (a) and (b) under storage, said gas being released into microbubbles at the time when the mixture is used for injection.

The tensides used in component (a) of U.S. Pat. No. 4,466,442 comprise lecithins; esters and ethers of fatty acids and fatty alcohols with polyoxyethylene and polyoxyethylated polyols like sorbitol, glycols and glycerol, cholesterol; and polyoxy-ethylene-polyoxypropylene polymers. The viscosity raising and stabilizing compounds include for instance mono- and polysaccharides (glucose, lactose, sucrose, dextran, sorbitol); polyols, e.g., glycerol, polyglycols; and polypeptides like proteins, gelatin, oxypolygelatin, plasma protein and the like.

In a typical preferred example of this latter document, equivalent volumes of (a) a 0.5% by weight aqueous solution of Pluronics® F-68 (a polyoxypropylene-polyoxyethylene polymer) and (b) a 10% lactose solution are vigorously shaken together under sterile conditions (closed vials) to provide a suspension of microbubbles ready for use as an ultrasonic contrast agent and lasting for at least 2 minutes. About 50% of the bubbles had a size below 50 $\mu$m.

Although the achievements of the prior art have merit, they suffer from several drawbacks which strongly limit their practical use by doctors and hospitals, namely their relatively short life-span (which makes test reproducibility difficult), relative low initial bubble concentration (the number of bubbles rarely exceeds $10^4$–$10^5$ bubbles/ml and the count decreases rapidly with time) and poor reproducibility of the initial bubble count from test to test (which also makes comparisons difficult). Also it is admitted that for efficiently imaging certain organs, e.g., the left heart, bubbles smaller than 50 $\mu$m, preferably in the range of 0.5–10 $\mu$m, are required; with larger bubbles, there are risks of clots and consecutive emboly.

Furthermore, the compulsory presence of solid microparticles or high concentrations of electrolytes and other relatively inert solutes in the carrier liquid may be undesirable physiologically in some cases. Finally, the suspensions are totally unstable under storage and cannot be marketed as such; hence great skill is required to prepare the microbubbles at the right moment just before use.

Of course there exists stable suspensions of microcapsules, i.e., microballoons with a solid, air-sealed rigid polymeric membrane which perfectly resist for long storage periods in suspension, which have been developed to remedy this shortcoming (see for instance K. J. Widder, EP-A-0324938); however the properties of microcapsules in which a gas is entrapped inside solid membrane vesicles essentially differ from that of the gas microbubbles of the present invention and belong to a different kind of art; for instance while the gas microbubbles discussed here will simply escape or dissolve in the blood-stream when the stabilizers in the carrier liquid are excreted or metabolized, the solid polymer material forming the walls of the aforementioned micro-balloons must eventually be disposed of by the organism being tested which may impose a serious afterburden upon it. Also capsules with solid, non-elastic membrane may break irreversibly under variations of pressure.

STABILIZED MICROBUBBLE COMPOSITIONS OF THE INVENTION

Figure 1:
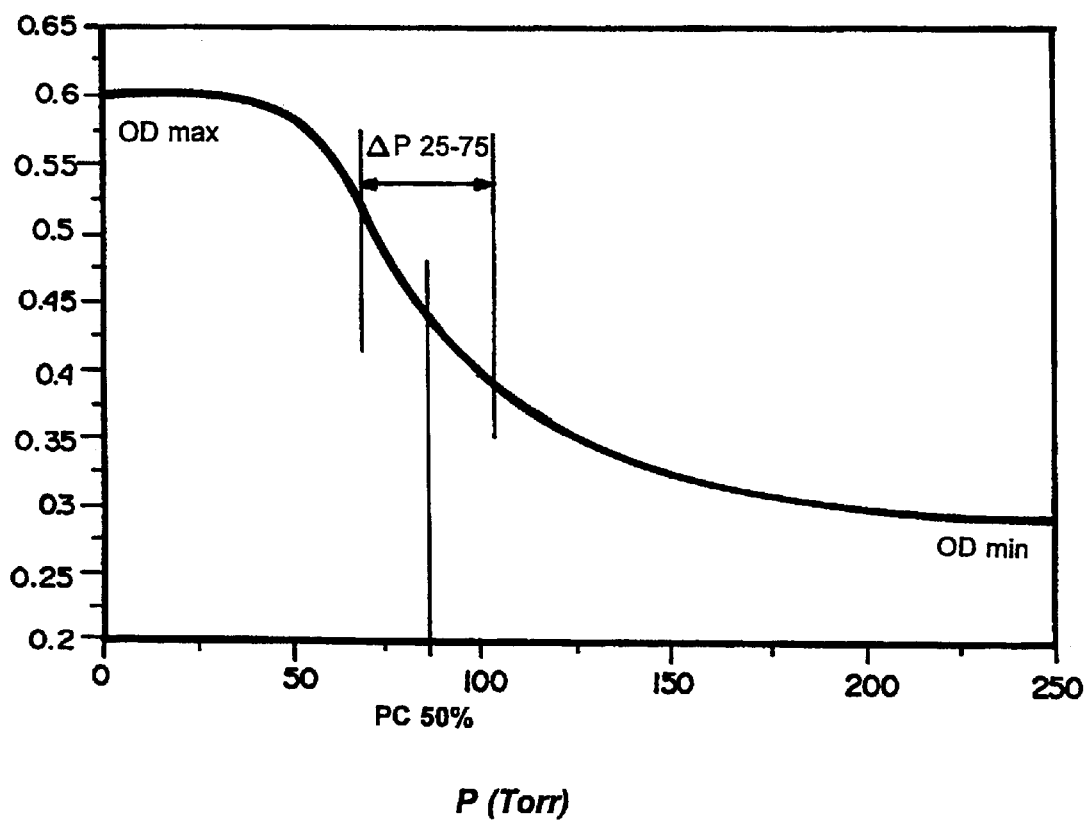
FIG. 1 is a diagram illustrating bubble concentration (bubble count), expressed in terms of optical density in the aforementioned range, and the pressure applied over the bubble suspension based on the data from the experiments reported in Example 15.

The compositions of the present invention fully remedy the aforementioned pitfalls.

The term "lamellar form" defining the condition of at least a portion of the surfactant or surfactants of the present composition indicates that the surfactants, in strong contrast with the microparticles of the prior art (for instance EP-A-0123235), are in the form of thin films involving one or more molecular layers (in laminate form). Converting film forming surfactants into lamellar form can easily be done for instance by high pressure homogenization or by sonication under acoustical or ultrasonic frequencies. In this connection, it should be pointed out that the existence of liposomes is a well known and useful illustration of cases in which surfactants, more particularly lipids, are in lamellar form.

Liposome solutions are aqueous suspensions of microscopic vesicles, generally spherically shaped, which hold substances encapsulated therein. These vesicles are usually formed of one or more concentrically arranged layers (lamellae) of amphipathic compounds, i.e., compounds having a lipophobic hydrophilic moiety and a lipophilic hydrophobic moiety. See for instance "Liposome Methodology", Ed. L. D. Leserman et al, Inserm 136, 2–8 (May 1982). Many surfactants or tensides, including lipids, particularly phospholipids, can be laminarized to correspond to this kind of structure. In this invention, one preferably uses the lipids commonly used for making liposomes, for instance the lecithins and other tensides disclosed in more detail hereafter, but this does in no way preclude the use of other surfactants provided they can be formed into layers or films.

It is important to note that no confusion should be made between the microbubbles of this invention and the disclosure of Ryan (U.S. Pat. No. 4,900,540) reporting the use of air or gas filled liposomes for echography. In this method Ryan encapsulates air or a gas within liposomic vesicles; in embodiments of the present invention microbubbles of air or a gas are formed in a suspension of liposomes (i.e., liquid filled liposomes) and the liposomes apparently stabilize the microbubbles. In Ryan, the air is inside the liposomes, which means that within the bounds of the presently used terminology, the air filled liposomes of Ryan belong to the class of microballoons and not to that of the microbubbles.

Practically, to achieve the suspensions of microbubbles according to the invention, one may start with liposomes suspensions or solutions prepared by any technique reported in the prior art, with the obvious difference that in the present case the liposomic vesicles are preferably "unloaded", i.e., they do not need to keep encapsulated therein any foreign material other than the liquid of suspension as is normally the object of classic liposomes. Hence, preferably, the liposomes of the present invention will contain an aqueous phase identical or similar to the aqueous phase of the solution itself. Then air or a gas is introduced into the liposome solution so that a suspension of microbubbles will form, said suspension being stabilized by the presence of the surfactants in lamellar form. Notwithstanding, the material making the liposome walls can be modified within the scope of the present invention, for instance by covalently grafting thereon foreign molecules designed for specific purposes as will be explained later.

The preparation of liposome solutions has been abundantly discussed in many publications, e.g., U.S. Pat. No. 4,224,179 and WO-A-88/09165 and all citations mentioned therein. This prior art is used here as reference for exemplifying the various methods suitable for converting film forming tensides into lamellar form. Another basic reference by M. C. Woodle and D. Papahadjopoulos is found in "Methods in Enzymology" 171 (1989), 193.

For instance, in a method disclosed in D. A. Tyrrell et al, Biochimica & Biophysica Acta 457 (1976), 259–302, a mixture of a lipid and an aqueous liquid carrier is subjected to violent agitation and thereafter sonicated at acoustic or ultrasonic frequencies at room or elevated temperature. In the present invention, it has been found that sonication without agitation is convenient. Also, an apparatus for making liposomes, a high pressure homogenizer such as the Microfluidizer®, which can be purchased from Microfluidics Corp., Newton, Mass. 02164 USA, can be used advantageously. Large volumes of liposome solutions can be prepared with this apparatus under pressures which can reach 600–1200 bar.

In another method, according to the teaching of GB-A-2,134,869 (Squibb), microparticles (10 $\mu$m or less) of a hydrosoluble carrier solid (NaCl, sucrose, lactose and other carbohydrates) are coated with an amphipathic agent; the dissolution of the coated carrier in an aqueous phase will yield liposomic vesicles. In GB-A-2,135,647 insoluble particles, e.g., glass or resin microbeads are coated by moistening in a solution of a lipid in an organic solvent followed by removal of the solvent by evaporation. The lipid coated microbeads are thereafter contacted with an aqueous carrier phase, whereby liposomic vesicles will form in that carrier phase.

The introduction of air or gas into a liposome solution in order to form therein a suspension of microbubbles can be effected by usual means, inter alia by injection, that is, forcing said air or gas through tiny orifices into the liposome solution, or simply dissolving the gas in the solution by applying pressure and thereafter suddenly releasing the pressure. Another way is to agitate or sonicate the liposome solution in the presence of air or an entrappable gas. Also one can generate the formation of a gas within the solution of liposomes itself, for instance by a gas releasing chemical reaction, e.g., decomposing a dissolved carbonate or bicarbonate by acid. The same effect can be obtained by dissolving under pressure a low boiling liquid, for instance butane, in the aqueous phase and thereafter allowing said liquid to boil by suddenly releasing the pressure.

Notwithstanding, an advantageous method is to contact the dry surfactant in lamellar or thin film form with air or an adsorbable or entrappable gas before introducing said surfactant into the liquid carrier phase. In this regard, the method can be derived from the technique disclosed in GB-A-2,135,647, i.e., solid microparticles or beads are dipped in a solution of a film forming surfactant (or mixture of surfactants) in a volatile solvent, after which the solvent is evaporated and the beads are left in contact with air (or an adsorbable gas) for a time sufficient for that air to become superficially bound to the surfactant layer. Thereafter, the beads coated with air filled surfactant are put into a carrier liquid, usually water with or without additives, whereby air bubbles will develop within the liquid by gentle mixing, violent agitation being entirely unnecessary. Then the solid beads can be separated, for instance by filtration, from the microbubble suspension which is remarkably stable with time.

Needless to say that, instead of insoluble beads or spheres, one may use as supporting particles water soluble materials like that disclosed in GB-A-2,134,869 (carbohydrates or hydrophilic polymers), whereby said supporting particles will eventually dissolve and final separation of a solid becomes unnecessary. Furthermore in this case, the material of the particles can be selected to eventually act as stabilizer or viscosity enhancer wherever desired.

In a variant of the method, one may also start with dehydrated liposomes, i.e., liposomes which have been prepared normally by means of conventional techniques in the form of aqueous solutions and thereafter dehydrated by usual means, e.g., such as disclosed in U.S. Pat. No. 4,229, 360 also incorporated herein by reference. One of the methods for dehydrating liposomes recommended in this reference is freeze-drying (lyophilization), i.e., the liposome solution is frozen and dried by evaporation (sublimation) under reduced pressure. Prior to effecting freeze-drying, a hydrophilic stabilizer compound is dissolved in the solution, for instance a carbohydrate like lactose or sucrose or a hydrophilic polymer like dextran, starch, PVP, PVA and the like. This is useful in the present invention since such hydrophilic compounds also aid in homogenizing the microbubbles size distribution and enhance stability under storage. Actually making very dilute aqueous solutions (0.1–10% by weight) of freeze-dried liposomes stabilized with, for instance, a 5:1 to 10:1 weight ratio of lactose to lipid enables to produce aqueous microbubbles suspensions counting $10^8$–$10^9$ microbubbles/ml (size distribution mainly 0.5–10 μm) which are stable for at least a month (and probably much longer) without significant observable change. And this is obtained by simple dissolution of the air-stored dried liposomes without shaking or any violent agitation. Furthermore, the freeze-drying technique under reduced pressure is very useful because it permits, after drying, to restore the pressure above the dried liposomes with any entrappable gas, i.e., nitrogen, $CO_2$, argon, methane, freon, etc., whereby after dissolution of the liposomes processed under such conditions suspensions of microbubbles containing the above gases are obtained.

Microbubbles suspensions formed by applying gas pressure on a dilute solution of laminated lipids in water (0.1–10% by weight) and thereafter suddenly releasing the pressure have an even higher bubble concentration, e.g., in the order of $10^{10}$–$10^{11}$ bubbles/ml. However, the average bubble size is somewhat above 10 μm, e.g., in the 10–50 μm range. In this case, bubble size distribution can be narrowed by centrifugation and layer decantation.

The tensides or surfactants which are convenient in this invention can be selected from all amphipathic compounds capable of forming stable films in the presence of water and gases. The preferred surfactants which can be laminarized include the lecithins (phosphatidyl-choline) and other phospholipids, inter alia phosphatidic acid (PA), phosphatidylinositol, phosphatidylethanolamine (PE), phosphatidylserine (PS), phosphatidylglycerol (PG), cardiolipin (CL), sphingomyelins, the plasmogens, the cerebrosides, etc. Examples of suitable lipids are the phospholipids in general, for example, natural lecithins, such as egg lecithin or soya bean lecithin, or synthetic lecithins such as saturated synthetic lecithins, for example, dimyristoylphosphatidylcholine, dipalmitoylphosphatidylcholine or distearoylphosphatidylcholine or unsaturated synthetic lecithins, such as dioleylphosphatidylcholine or dilinoleylphosphatidylcholine, with egg lecithin or soya bean lecithin being preferred. Additives like cholesterol and other substances (see below) can be added to one or more of the foregoing lipids in proportions ranging from zero to 50% by weight.

Such additives may include other surfactants that can be used in admixture with the film forming surfactants and most of which are recited in the prior art discussed in the introduction of this specification. For instance, one may cite free fatty acids, esters of fatty acids with polyoxyalkylene compounds like polyoxypropylene glycol and polyoxyalkylene glycol; ethers of fatty alcohols with polyoxyalkylene glycols; esters of fatty acids with polyoxyalklated sorbitan; soaps; glycerol-polyalkylene stearate; glycerol-polyoxyethylene ricinoleate; homo- and copolymers of polyalkylene glycols; polyethoxylated soya-oil and castor oil as well as hydrogenated derivatives; ethers and esters of sucrose or other carbohydrates with fatty acids, fatty alcohols, these being optionally polyoxyalkylated; mono- di and triglycerides of saturated or unsaturated fatty acids; glycerides of soya-oil and sucrose. The amount of the non-film forming tensides or surfactants can be up to 50% by weight of the total amount of surfactants in the composition but is preferably between zero and 30%.

The total amount of surfactants relative to the aqueous carrier liquid is best in the range of 0.01 to 25% by weight but quantities in the range 0.5–5% are advantageous because one always tries to keep the amount of active substances in an injectable solution as low as possible, this being to minimize the introduction of foreign materials into living beings even when they are harmless and physiologically compatible.

Further optional additives to the surfactants include:
a) substances which are known to provide a negative charge on liposomes, for example, phosphatidic acid, phosphatidyl-glycerol or dicetyl phosphate;
b) substances known to provide a positive charge, for example, stearyl amine, or stearyl amine acetate;
c) substances known to affect the physical properties of the lipid films in a more desirable way; for example, capro-lactam and/or sterols such as cholesterol, ergosterol, phytosterol, sitosterol, sitosterol pyroglutamate, 7-dehydro-cholesterol or lanosterol, may affect lipid films rigidity;
d) substances known to have antioxidant properties to improve the chemical stability of the components in the suspensions, such as tocopherol, propyl gallate, ascorbyl palmitate, or butylated hydroxy toluene.

The aqueous carrier in this invention is mostly water with possibly small quantities of physiologically compatible liquids such as isopropanol, glycerol, hexanol and the like (see for instance EP-A-052575). In general the amount of the organic hydrosoluble liquids will not exceed 5–10% by weight.

The present composition may also contain dissolved or suspended therein hydrophilic compounds and polymers defined generally under the name of viscosity enhancers or stabilizers. Although the presence of such compounds is not compulsory for ensuring stability to the air or gas bubbles with time in the present dispersions, they are advantageous to give some kind of "body" to the solutions. When desired, the upper concentrations of such additives when totally innocuous can be very high, for instance up to 80–90% by weight of solution with Iopamidol and other iodinated X-ray contrast agents. However, with the viscosity enhancers like for instance sugars, e.g., lactose, sucrose, maltose, galactose, glucose, etc. or hydrophilic polymers like starch, dextran, polyvinyl alcohol, polyvinyl-pyrrolidone, dextrin, xanthan or partly hydrolyzed cellulose oligomers, as well as proteins and polypeptides, the concentrations are best between about 1 and 40% by weight, a range of about 5–20% being preferred.

Like in the prior art, the injectable compositions of this invention can also contain physiologically acceptable electrolytes; an example is an isotonic solution of salt.

The present invention naturally also includes dry storable pulverulent blends which can generate the present microbubble containing dispersions upon simple admixing with water or an aqueous carrier phase. Preferably such dry blends or formulations will contain all solid ingredients necessary to provide the desired microbubbles suspensions upon the simple addition of water, i.e., principally the surfactants in lamellar form containing trapped or adsorbed therein the air or gas required for microbubble formation, and accessorily the other non-film forming surfactants, the viscosity enhancers and stabilizers and possibly other optional additives. As said before, the air or gas entrapment by the laminated surfactants occurs by simply exposing said surfactants to the air (or gas) at room or superatmospheric pressure for a time sufficient to cause said air or gas to become entrapped within the surfactant. This period of time can be very short, e.g., in the order of a few seconds to a few minutes although over-exposure, i.e., storage under air or under a gaseous atmosphere is in no way harmful. What is important is that air can well contact as much as possible of the available surface of the laminated surfactant, i.e., the dry material should preferably be in a "fluffy" light flowing condition. This is precisely this condition which results from the freeze-drying of an aqueous solution of liposomes and hydrophilic agent as disclosed in U.S. Pat. No. 4,229,360.

In general, the weight ratio of surfactants to hydrophilic viscosity enhancer in the dry formulations will be in the order of 0.1:10 to 10:1, the further optional ingredients, if any, being present in a ratio not exceeding 50% relative to the total of surfactants plus viscosity enhancers.

The dry blend formulations of this invention can be prepared by very simple methods. As seen before, one preferred method is to first prepare an aqueous solution in which the film forming lipids are laminarized, for instance by sonication, or using any conventional technique commonly used in the liposome field, this solution also containing the other desired additives, i.e., viscosity enhancers, non-film forming surfactants, electrolyte, etc., and thereafter freeze drying to a free flowable powder which is then stored in the presence of air or an entrappable gas.

The dry blend can be kept for any period of time in the dry state and sold as such. For putting it into use, i.e., for preparing a gas or air microbubble suspension for ultrasonic imaging, one simply dissolves a known weight of the dry pulverulent formulation in a sterile aqueous phase, e.g., water or a physiologically acceptable medium. The amount of powder will depend on the desired concentration of bubbles in the injectable product, a count of about $10^8$–$10^9$ bubbles/ml being generally that from making a 5–20% by weight solution of the powder in water. But naturally this figure is only indicative, the amount of bubbles being essentially dependent on the amount of air or gas trapped during manufacture of the dry powder. The manufacturing steps being under control, the dissolution of the dry formulations will provide microbubble suspensions with well reproducible counts.

The resulting microbubble suspensions (bubble in the 0.5–10 $\mu$m range) are extraordinarily stable with time, the count originally measured at start staying unchanged or only little changed for weeks and even months; the only observable change is a kind of segregation, the larger bubbles (around 10 $\mu$m) tending to rise faster than the small ones.

It has also been found that the microbubbles suspensions of this invention can be diluted with very little loss in the number of microbubbles to be expected from dilution, i.e., even in the case of high dilution ratios, e.g., 1/$10^2$ to 1/$10^4$, the microbubble count reduction accurately matches with the dilution ratio. This indicates that the stability of the bubbles depends on the surfactant in lamellar form rather than on the presence of stabilizers or viscosity enhancers like in the prior art. This property is advantageous in regard to imaging test reproducibility as the bubbles are not affected by dilution with blood upon injection into a patient.

Another advantage of the bubbles of this invention versus the microbubbles of the prior art surrounded by a rigid but breakable membrane which may irreversibly fracture under stress is that when the present suspensions are subject to sudden pressure changes, the present bubbles will momentarily contract elastically and then resume their original shape when the pressure is released. This is important in clinical practice when the microbubbles are pumped through the heart and therefore are exposed to alternating pressure pulses.

The reasons why the microbubbles in this invention are so stable are not clearly understood. Since to prevent bubble escape the buoyancy forces should equilibrate with the retaining forces due to friction, i.e., to viscosity, it is theorized that the bubbles are probably surrounded by the laminated surfactant. Whether this laminar surfactant is in the form of a continuous or discontinuous membrane, or even as closed spheres attached to the microbubbles, is for the moment unknown but under investigation. However the lack of a detailed knowledge of the phenomena presently involved does not prelude full industrial operability of the present invention.

The bubble suspensions of the present invention are also useful in other medical/diagnostic applications where it is desirable to target the stabilized microbubbles to specific sites in the body following their injection, for instance to thrombi present in blood vessels, to atherosclerotic lesions (plaques) in arteries, to tumor cells, as well as for the diagnosis of altered surfaces of body cavities, e.g., ulceration sites in the stomach or tumors of the bladder. For this, one can bind monoclonal antibodies tailored by genetic engineering, antibody fragments or polypeptides designed to mimic antibodies, bioadhesive polymers, lectins and other site-recognizing molecules to the surfactant layer stabilizing the microbubbles. Thus monoclonal antibodies can be bound to phospholipid bilayers by the method described by L. D. Leserman, P. Machy and J. Barbet ("Liposome Technology vol. III" p. 29 ed. by G. Gregoriadis, CRC Press 1984). In another approach a palmitoyl antibody is first synthesized and then incorporated in phospholipid bilayers following L. Huang, A. Huang and S. J. Kennel ("Liposome Technology vol. III" p. 51 ed. by G. Gregoriadis, CRC Press 1984). Alternatively, some of the phospholipids used in the present invention can be carefully selected in order to obtain preferential uptake in organs or tissues or increased half-life in blood. Thus GM1 gangliosides- or phosphatidylinositol-containing liposomes, preferably in addition to cholesterol, will lead to increased, half-lifes in blood after intravenous administration in analogy with A. Gabizon, D. Papahadjopoulos, Proc. Natl Acad. Sci USA 85 (1988) 6949.

The gases in the microbubbles of the present invention can include, in addition to current innocuous physiologically acceptable gases like $CO_2$, nitrogen, $N_2O$, methane, butane, freon and mixtures thereof, radioactive gases such as $^{133}$Xe or $^{81}$Kr are of particular interest in nuclear medicine for blood circulation measurements, for lung scintigraphy etc.

The invention described up until this point can be further elucidated by the description of the following representative (but not limiting) embodiments, numbered 1–27:

1. A composition adapted for injection into the bloodstream and body cavities of living beings, e.g., for the purpose of ultrasonic echography consisting of a suspension of air or gas microbubbles in a physiologically acceptable aqueous carrier phase comprising from about 0.01 to about 20% by weight of one or more dissolved or dispersed surfactants, characterized in that at least one of the surfactants is a film forming surfactant present in the composition at least partially in lamellar or laminar form.

2. The composition of embodiment 1, characterized in that the lamellar surfactant is in the form of mono- or pluri-molecular membrane layers.

3. The composition of embodiment 1, characterized in that the lamellar surfactant is in the form of liposome vesicles.

4. The composition of embodiment 1, characterized in that it essentially consists of a liposome solution containing air or gas microbubbles developed therein.

5. The composition of embodiment 4, characterized in that the size of most of both liposomes and microbubbles is below 50 μm, preferably below 10 μm.

6. The composition of embodiment 1, containing about $10^8$–$10^9$ bubbles of 0.5–10 μm size/ml, said concentration showing little or substantially no variability under storage for at least a month.

7. The composition of embodiment 1, characterized in that the surfactants are selected from phospholipids including the lecithins such as phosphatidic acid, phosphatidylcholine, phosphatidylethanolamine, phosphatidylserine, phosphatidylglycerol, phosphatidylinositol, cardiolipin and sphyngomyelin.

8. The composition of embodiment 7, characterized in further containing substances affecting the properties of liposomes selected form phosphatidylglycerol, dicetylphosphate, cholesterol, ergosterol, phytosterol, sitosterol, lanosterol, tocopterol, propyl gallate, ascorbyl palmitate and butylated hydroxytoluene.

9. The composition of embodiment 1, further containing dissolved viscosity enhancers or stabilizers selected from linear and cross-linked poly- and oligo-saccharides, sugars, hydrophilic polymers and iodinated compounds such as Iopamidol in a weight ratio to the surfactants comprised between about 1:5 to 100:1.

10. The composition of embodiment 1, in which the surfactants comprise up to 50% by weight of non-laminar surfactants selected from fatty acids, esters, and ethers of fatty acids and alcohols with polyols such as polyalkylene glycols, polyalkylenated sugars and other carbohydrates, and polyalkylenated glycerol.

11. A method for the preparation of the suspensions of embodiment 1, characterized by the following steps:
  (a) selecting at least one film forming surfactant and converting it into lamellar form;
  (b) contacting the surfactant in lamellar form with air or an adsorbable or entrappable gas for a time sufficient for that air or gas to become bound by said surfactant; and
  (c) admixing the surfactant in lamellar form with an aqueous liquid carrier, whereby a stable dispersion of air or gas microbubbles in said liquid carrier will result.

12. The method of embodiment 11, in which step (c) is brought about before step (b), the latter being effected by introducing pressurized air or gas into the liquid carrier and thereafter releasing the pressure.

13. The method of embodiment 11, in which step (c) is brought about by gentle mixing of the components, no shaking being necessary, whereby the air or gas bound to the lamellar surfactant in step (b) will develop into a suspension of stable microbubbles.

14. The method of embodiments 11 or 12, in which the liquid carrier contains dissolved therein stabilizer compounds selected from hydrosoluble proteins, polypeptides, sugars, poly- and oligo-saccharides and hydrophilic polymers.

15. The method of embodiment 11, in which the conversion of step (a) is effected by coating the surfactant onto particles of soluble or insoluble materials; step (b) is effected by letting the coated particles stand for a while under air or a gas; and step (c) is effected by admixing the coated particles with an aqueous liquid carrier.

16. The method of embodiment 11, in which the conversion of step (a) is effected by sonicating or homogenizing under high pressure an aqueous solution of film forming lipids, this operation leading, at least partly, to the formation of liposomes.

17. The method of embodiment 16, in which step (b) is effected by freeze-drying the liposome containing solution, the latter optionally containing hydrophilic stabilizers and contacting the resulting freeze-dried product with air or gas for a period of time.

18. The method of embodiments 16 and 17, in which the water solution of film forming lipids also contains viscosity enhancers or stabilizers selected from hydrophilic polymers and carbohydrates in weight ratio relative to the lipids comprised between 1:5 and 100:1.

19. A dry pulverulent formulation which, upon dissolution in water, will form an aqueous suspension of microbubbles for ultrasonic echography, characterized in containing one or more film forming surfactants in laminar form and hydrosoluble stabilizers.

20. The dry formulation of embodiment 19, in which the surfactants in laminar form are in the form of fine layers deposited on the surface of soluble or insoluble solid particulate material.

21. The dry formulation of embodiment 20, in which the insoluble solid particles are glass or polymer beads.

22. The dry formulation of embodiment 20, in which the soluble particles are made of hydrosoluble carbohydrates, polysaccharides, synthetic polymers, albumin, gelatin or Iopamidol.

23. The dry formulation of embodiment 19, which comprises freeze-dried liposomes.

24. The use of the injectable composition of embodiment 1 for ultrasonic echography.

25. The use of the injectable composition of embodiments 1–10 for transporting in the blood-stream or body cavities bubbles of foreign gases active therapeutically or diagnostically.

26. The composition of embodiment 4, in which the surfactant comprises, bound thereto, bioactive species designed for specific targeting purposes, e.g., for immobilizing the bubbles in specifically defined sites in the circulatory system, or in organs, or in tissues.

27. The composition of embodiment 4, in which the surfactant comprises, bound thereto, bioactive species selected from monoclonal antibodies, antibody fragments or polypeptides designed to mimic antibodies, bioadhesive polymers, lectins and other receptor recognizing molecules.

The following Examples further illustrate the invention from a practical standpoint.

Echogenic Measurements

Echogenicity measurements were performed in a pulse-echo system made of a plexiglas specimen holder (diameter 30 mm) and a transducer holder immersed in a constant temperature water bath, a pulser-receiver (Accutron M3010S) with for the receiving part an external pre-amplifier with a fixed gain of 40 dB and an internal amplifier with adjustable gain from −40 to +40 dB. A 10 MHz low-pass filter was inserted in the receiving part to improve the signal to noise ratio. The A/D board in the IBM PC was a Sonotek STR 832. Measurements were carried out at 2.25, 3.5, 5 and 7.5 MHz.

EXAMPLE 1

A liposome solution (50 mg lipids per ml) was prepared in distilled water by the REV method (see F. Szoka Jr. and D. Papahadjopoulos, Proc. Natl. Acad. Sci. USA 75 (1978) 4194) using hydrogenated soya lecithin (NC 95 H, Nattermann Chemie, Koln, W. Germany) and dicetylphosphate.in a molar ratio 9/1. This liposome preparation was extruded at 65° C. (to calibrate the vesicle size) through a 1 $\mu$m polycarbonate filter (Nucleopore). Two ml of this solution were admixed with 5 ml of a 75% iopamidol solution in water and 0.4 ml of air and the mixture was forced back and forth through a two syringe system as disclosed in DE-A-3529195, while maintaining continuously a slight overpressure. This resulted in the formation of a suspension of microbubbles of air in the liquid ($10^5$–$10^6$ bubbles per ml, bubble size 1–20 $\mu$m as estimated by light microscopy) which was stable for several hours at room temperature. This suspension gave a strong echo signal when tested by ultrasonic echography at 7.5, 5, 3.5 and 2.25 MHz.

EXAMPLE 2

A distilled water solution (100 ml) containing by weight 2% of hydrogenated soya lecithin and dicetylphosphate in a 9/1 molar ratio was sonicated for 15 min at 60°–65° C. with a Branson probe sonifier (Type 250). After cooling, the solution was centrifuged for 15 min at 10,000 g and the supernatant was recovered and lactose added to make a 7.5% b.w. solution. The solution was placed in a tight container in which a pressure of 4 bar of nitrogen was established for a few minutes while shaking the container. Afterwards, the pressure was released suddenly whereby a highly concentrated bubble suspension was obtained ($10^{10}$–$10^{11}$ bubbles/ml). The size distribution of the bubbles was however wider than in Example 1, i.e., from about 1 to 50 $\mu$m. The suspension was very stable but after a few days a segregation occurred in the standing phase, the larger bubbles tending to concentrate in the upper layers of the suspension.

EXAMPLE 3

Twenty g of glass beads (diameter about 1 mm) were immersed into a solution of 100 mg of dipalmitoylphosphatidylcholine (Fluka A. G. Buchs) in 10 ml of chloroform. The beads were rotated under reduced pressure in a rotating evaporator until all $CHCl^3$ had escaped. Then the beads were further rotated under atmospheric pressure for a few minutes and 10 ml of distilled water were added. The beads were removed and a suspension of air microbubbles was obtained which was shown to contain about $10^6$ bubbles/ml after examination under the microscope. The average size of the bubbles was about 3–5 $\mu$m. The suspension was stable for several days at least.

EXAMPLE 4

A hydrogenated soya lecithin/dicetylphosphate suspension in water was laminarized using the REV technique as described in Example 1. Two ml of the liposome preparation were added to 8 ml of 15% maltose solution in distilled water. The resulting solution was frozen at −30° C., then lyophilized under 0.1 Torr. Complete sublimation of the ice was obtained in a few hours. Thereafter, air pressure was restored in the evacuated container so that the lyophilized powder became saturated with air in a few minutes.

The dry powder was then dissolved in 10 ml of sterile water under gentle mixing, whereby a microbubble suspension ($10^8$–$10^9$ microbubbles per ml, dynamic viscosity <20 mPa.s) was obtained. This suspension containing mostly bubbles in the 1–5 $\mu$m range was stable for a very long period, as numerous bubbles could still be detected after 2 months standing. This microbubble suspension gave a strong response in ultrasonic echography. If in this example the solution is frozen by spraying in air at −30° to −70° C. to obtain a frozen snow instead of a monolithic block and the snow is then evaporated under vacuum, excellent results are obtained.

EXAMPLE 5

Two ml samples of the liposome solution obtained as described in Example 4 were mixed with 10 ml of an 5% aqueous solution of gelatin (sample 5A), human albumin (sample 5B), dextran (sample 5C) and iopamidol (sample 5D). All samples were lyophilized. After lyophilization and introduction of air, the various samples were gently mixed with 20 ml of sterile water. In all cases, the bubble concentration was above $10^8$ bubbles per ml and almost all bubbles were below 10 $\mu$m. The procedure of the foregoing Example was repeated with 9 ml of the liposome preparation (450 mg of lipids) and only one ml of a 5% human albumin solution. After lyophilization, exposure to air and addition of sterile water (20 ml), the resulting solution contained $2\times10^8$ bubbles per ml, most of the them below 10 $\mu$m.

EXAMPLE 6

Lactose (500 mg), finely milled to a particle size of 1–3 $\mu$m, was moistened with a chloroform (5 ml) solution of 100 mg of dimyristoylphosphatidylcholine/cholesterol/dipalmitoylphosphatidic acid (from Fluka) in a molar ratio of 4:1:1 and thereafter evaporated under vacuum in a rotating evaporator. The resulting free flowing white powder was rotated a few minutes under nitrogen at normal pressure and thereafter dissolved in 20 ml of sterile water. A microbubble suspension was obtained with about $10^5$–$10^6$ microbubbles per ml in the 1–10 $\mu$m size range as ascertained by observation under the microscope. In this Example, the weight ratio of coated surfactant to water-soluble carrier was 1:5. Excellent results ($10^7$–$10^8$ microbubbles/ml) are also obtained when reducing this ratio to lower values, i.e., down to 1:20, which will actually increases the surfactant efficiency for the intake of air, that is, this will decrease the weight of surfactant necessary for producing the same bubble count.

EXAMPLE 7

An aqueous solution containing 2% of hydrogenated soya lecithin and 0.4% of Pluronic® F68 (a non ionic polyoxyethylenepolyoxypropylene copolymer surfactant) was sonicated as described in Example 2. After cooling and centrifugation, 5 ml of this solution were added to 5 ml of a 15% maltose solution in water. The resulting solution was frozen at −30° C. and evaporated under 0.1 Torr. Then air pressure was restored in the vessel containing the dry powder. This was left to stand in air for a few seconds, after which it was used to make a 10% by weight aqueous solution which showed under the microscope to be a suspension of very tiny bubbles (below 10 μm); the bubble concentration was in the range of $10^7$ bubbles per ml. This preparation gave a very strong response in ultrasonic echography at 2.25, 3.5, 5 and 7.5 MHz.

EXAMPLE 8

Two-dimensional echocardiography was performed in an experimental dog following peripheral vein injection of 0.1–2 ml of the preparation obtained in Example 4. Opacification of the left heart with clear outlining of the endocardium was observed, thereby confirming that the microbubbles (or at least a significant part of them) were able to cross the pulmonary capillary circulation.

EXAMPLE 9

A phospholipid/maltose lyophilized powder was prepared as described in Example 4. However, at the end of the lyophilization step, a $^{133}$Xe containing gas mixture was introduced in the evacuated container instead of air. A few minutes later, sterile water was introduced and after gentle mixing a microbubble suspension containing $^{133}$Xe in the gas phase was produced. This microbubble suspension was injected into living bodies to undertake investigations requiring use of $^{133}$Xe as tracer. Excellent results were obtained.

EXAMPLE 10

Comparative

In U.S. Pat. No. 4,900,540, Ryan et al disclose gas filled liposomes for ultrasonic investigations. According to the citation, liposomes are formed by conventional means but with the addition of a gas or gas precursor in the aqueous composition forming the liposome core (col. 2, lines 15–27).

Using a gas precursor (bicarbonate) is detailed in Examples 1 and 2 of the reference. Using an aqueous carrier with an added gas for encapsulating the gas in the liposomes (not exemplified by Ryan et al) will require that the gas be in the form of very small bubbles, i.e., of size similar or smaller than the size of the liposome vesicles.

Aqueous media in which air can be entrapped in the form of very small bubbles (2.5–5 μm) are disclosed in M. W. Keller et al, J. Ultrasound Med. 5 (1986), 413–498.

A quantity of 126 mg of egg lecithin and 27 mg of cholesterol were dissolved in 9 ml of chloroform in a 200 ml round bottom flask. The solution of lipids was evaporated to dryness on a Rotavapor whereby a film of the lipids was formed on the walls of the flask. A 10 ml of a 50% by weight aqueous dextrose solution was sonicated for 5 min according to M. W. Keller et al (ibid) to generate air microbubbles therein and the sonicated solution was added to the flask containing the film of lipid, whereby hand agitation of the vessel resulted into hydration of the phospholipids and formation of multilamellar liposomes within the bubbles containing carrier liquid.

After standing for a while, the resulting liposome suspension was subjected to centrifugation under 5000 g for 15 min to remove from the carrier the air not entrapped in the vesicles. It was also expected that during centrifugation, the air filled liposomes would segregate to the surface by buoyancy.

After centrifugation the tubes were examined and showed a bottom residue consisting of agglomerated dextrose filled liposomes and a clear supernatant liquid with substantially no bubbles left. The quantity of air filled liposomes having risen by buoyancy was negligibly small and could not be ascertained.

EXAMPLE 11

Comparative

An injectable contrast composition was prepared according to Ryan (U.S. Pat. No. 4,900,540, col. 3, Example 1). Egg lecithin (126 mg) and cholesterol (27 mg) were dissolved in 9 ml of diethylether. To the solution were added 3 ml of 0.2 molar aqueous bicarbonate and the resulting two phase systems was sonicated until becoming homogeneous. The mixture was evaporated in a Rotavapor apparatus and 3 ml of 0.2 molar aqueous bicarbonate were added.

A 1 ml portion of the liposome suspension was injected into the jugular vein of an experimental rabbit, the animal being under condition for heart ultrasonic imaging using an Acuson 128-XP5 ultrasonic imager (7.5 transducer probe for imaging the heart). The probe provided a cross-sectional image of the right and left ventricles (mid-papillary muscle). After injection, a light and transient (a few seconds) increase in the outline of the right ventricle was observed. The effect was however much inferior to the effect observed using the preparation of Example 4. No improvement of the imaging of the left ventricle was noted which probably indicates that the $CO_2$ loaded liposomes did not pass the pulmonary capillaries barrier.

Further Methods of the Invention and Gases Used therein

Despite the many progresses achieved regarding the stability under storage of aqueous microbubble suspensions, this being either in the precursor or final preparation stage, there still remained until now the problem of vesicle durability when the suspensions are exposed to overpressure, e.g., pressure variations such as that occurring after injection in the blood stream of a patient and consecutive to heart pulses, particularly in the left ventricle. Actually, the present inventors have observed that, for instance in anaesthetized rabbits, the pressure variations are not sufficient to substantially alter the bubble count for a period of time after injection. In contrast, in dogs and human patients, typical microbubbles or microballoons filled with common gases such as air, methane or $CO_2$ will collapse completely in a matter of seconds after injection due to the blood pressure effect. It became hence important to solve the problem and to increase the useful life of suspensions of microbubbles and membrane bounded microballoons under pressure in order to ensure that echographic measurements can be performed in vivo safely and reproducibly.

It should be mentioned at this stage that another category of echogenic image enhancing agents has been proposed which resist overpressures as they consist of plain microspheres with a porous structure, such porosity containing air or a gas. Such microspheres are disclosed for instance in WO-A-91/12823 (Delta Biotechnology), EP-A-0327490 (Schering) and EP-A-0458079 (Hoechst). The drawback with the plain porous microspheres is that the encapsulated gas-filled free space is generally too small for good echogenic response and the spheres lack adequate elasticity. Hence the preference generally remains with the hollow microvesicles and a solution to the collapsing problem was searched.

This problem has now been solved by using gases or gas mixtures in conformity with the criteria outlined in the embodiments shown below. Briefly, it has been found that when the echogenic microvesicles are made in the presence of a gas, respectively are filled at least in part with a gas, having physical properties in conformity with the equation below, then the microvesicles remarkably resist pressure >60 Torr after injection for a time sufficient to obtain reproducible echographic measurements:

$$\frac{s_{gas}}{s_{air}} \times \frac{\sqrt{Mw_{air}}}{\sqrt{Mw_{gas}}} \leq 1$$

In the foregoing equation, "s" designates the solubilities in water expressed as the "Bunsen" coefficients, i.e., as volume of gas dissolved by unit volume of water under standard conditions (1 bar, 250° C.), and under partial pressure of the given gas of 1 atm (see the Gas Encyclopaedia, Elsevier 1976). Since, under such conditions and definitions, the solubility of air is .0167, and the square root of its average molecular weight (Mw) is 5.39, the above relation simplifies to:

$$s_{gas}/\sqrt{Mw_{gas}} \leq .0031$$

In the Examples to be found hereafter there is disclosed the testing of echogenic microbubbles and microballoons (see the Tables) filled with a number of different gases and mixtures thereof, and the corresponding resistance thereof to pressure increases, both in vivo and in vitro. In the Tables, the water solubility factors have also been taken from the aforecited Gas Encyclopaedia from "L'Air Liquid", Elsevier Publisher (1976).

The microvesicles in aqueous suspension containing gases according to the invention include most microbubbles and microballoons disclosed until now for use as contrast agents for echography. The preferred microballoons are those disclosed in EP-A-0324938, PCT/EP91/01706 and EP-A-0458745; the preferred microbubbles are those of the compositions disclosed herein (e.g., supra) and in PCT/EP91/00620; these microbubbles are advantageously formed from an aqueous liquid and a dry powder (microvesicle precursors) containing lamellarized freeze-dried phospholipids and stabilizers; the microbubbles are developed by agitation of this powder in admixture with the aqueous liquid carrier. The microballoons of EP-A-0458745 have a resilient interfacially precipitated polymer membrane of controlled porosity. They are generally obtained from emulsions into microdroplets of polymer solutions in aqueous liquids, the polymer being subsequently caused to precipitate from its solution to form a fibrogenic membrane at the droplet/liquid interface, which process leads to the initial formation of liquid-filled microvesicles, the liquid core thereof being eventually substituted by a gas.

In order to carry out the method of the present invention, i.e., to form or fill the microvesicles, whose suspensions in aqueous carriers constitute the desired echogenic additives, with the gases according to the foregoing relation, one can either use, as a first embodiment, a two step route consisting of (1) making the microvesicles from appropriate starting materials by any suitable conventional technique in the presence of any suitable gas, and (2) replacing this gas originally used (first gas) for preparing the microvesicles with a new gas (second gas) according to the invention (gas exchange technique).

Otherwise, according to a second embodiment, one can directly prepare the desired suspensions by suitable usual methods under an atmosphere of the new gas according to the invention.

If one uses the two-step route, the initial gas can be first removed from the vesicles (for instance by evacuation under suction) and thereafter replaced by bringing the second gas into contact with the evacuated product, or alternatively, the vesicles still containing the first gas can be contacted with the second gas under conditions where the second gas will displace the first gas from the vesicles (gas substitution). For instance, the vesicle suspensions, or preferably precursors thereof (precursors here may mean the materials the microvesicle envelopes are made of, or the materials which, upon agitation with an aqueous carrier liquid, will generate or develop the formation of microbubbles in this liquid), can be exposed to reduced pressure to evacuate the gas to be removed and then the ambient pressure is restored with the desired gas for substitution. This step can be repeated once or more times to ensure complete replacement of the original gas by the new one. This embodiment applies particularly well to precursor preparations stored dry, e.g., dry powders which will regenerate or develop the bubbles of the echogenic additive upon admixing with an amount of carrier liquid. Hence, in one preferred case where microbubbles are to be formed from an aqueous phase and dry laminarized phospholipids, e.g., powders of dehydrated lyophilized liposomes plus stabilizers, which powders are to be subsequently dispersed under agitation in a liquid aqueous carrier phase, it is advantageous to store this dry powder under an atmosphere of a gas selected according to the invention. A preparation of such kind will keep indefinitely in this state and can be used at any time for diagnosis, provided it is dispersed into sterile water before injection.

Otherwise, and this is particularly so when the gas exchange is applied to a suspension of microvesicles in a liquid carrier phase, the latter is flushed with the second gas until the replacement (partial or complete) is sufficient for the desired purpose. Flushing can be effected by bubbling from a gas pipe or, in some cases, by simply sweeping the surface of the liquid containing the vesicles under gentle agitation with a stream (continuous or discontinuous) of the new gas. In this case, the replacement gas can be added only once in the flask containing the suspension and allowed to stand as such for a while, or it can be renewed one or more times in order to assure that the degree of renewal (gas exchange) is more or less complete.

Alternatively, in a second embodiment as said before, one will effect the full preparation of the suspension of the echogenic additives starting with the usual precursors thereof (starting materials), as recited in the prior art and operating according to usual means of said prior art, but in the presence of the desired gases or mixture of gases according to the invention instead of that of the prior art which usually recites gases such as air, nitrogen, $CO_2$ and the like.

It should be noted that in general the preparation mode involving one first type of gas for preparing the microvesicles and, thereafter, substituting the original gas by a second kind of gas, the latter being intended to confer different echogenic properties to said microvesicles, has the following advantage: As will be best seen from the results in the Examples hereinafter, the nature of the gas used for making the microvesicles, particularly the microballoons with a polymer envelope, has a definitive influence on the overall size (i.e., the average mean diameter) of said microvesicles; for instance, the size of microballoons prepared under air with precisely set conditions can be accurately controlled to fall within a desired range, e.g., the 1 to 10 µm range suitable for echographying the left and right heart ventricles. This not so easy with other gases, particularly the gases in conformity with the requirements of the present invention; hence, when one wishes to obtain microvesicles in a given size range but filled with gases the nature of which would render the direct preparation impossible or very hard, one will much advantageously rely on the two-steps preparation route, i.e., one will first prepare the microvesicles with a gas allowing more accurate diameter and count control, and thereafter replace the first gas by a second gas by gas exchange.

In the description of the Experimental part that follows (Examples), gas-filled microvesicles suspended in water or other aqueous solutions have been subjected to pressures over that of ambient. It was noted that when the overpressure reached a certain value (which is generally typical for a set of microsphere parameters and working conditions like temperature, compression rate, nature of carrier liquid and its content of dissolved gas (the relative importance of this parameter will be detailed hereinafter), nature of gas filler, type of echogenic material, etc.), the microvesicles started to collapse, the bubble count progressively decreasing with further increasing the pressure until a complete disappearance of the sound reflector effect occurred. This phenomenon was better followed optically, (nephelometric measurements) since it is paralleled by a corresponding change in optical density, i.e., the transparency of the medium increases as the bubble progressively collapse. For this, the aqueous suspension of microvesicles (or an appropriate dilution thereof was placed in a spectrophotometric cell maintained at 25° C. (standard conditions) and the absorbance was measured continuously at 600 or 700 nm, while a positive hydrostatic overpressure was applied and gradually increased. The pressure was generated by means of a peristaltic pump (Gilson's Mini-puls) feeding a variable height liquid column connected to the spectrophotometric cell, the latter being sealed leak-proof. The pressure was measured with a mercury manometer calibrated in Torr. The compression rate with time was found to be linearly correlated with the pump's speed (rpm's). The absorbance in the foregoing range was found to be proportional to the microvesicle concentration in the carrier liquid.

The invention will now be further described with reference to FIG. 1 which is a graph which relates the bubble concentration (bubble count), expressed in terms of optical density in the aforementioned range, and the pressure applied over the bubble suspension. The data for preparing the graph are taken from the experiments reported in Example 15.

FIG. 1 shows graphically that the change of absorbance versus pressure is represented by a sigmoid-shaped curve. Up to a certain pressure value, the curve is nearly flat which indicates that the bubbles are stable. Then, a relatively fast absorbance drop occurs, which indicates the existence of a relatively narrow critical region within which any pressure increase has a rather dramatic effect on the bubble count. When all the microvesicles have disappeared, the curve levels off again. A critical point on this curve was selected in the middle between the higher and lower optical readings, i.e., intermediate between the "full"-bubble (OD max) and the "no"-bubble (OD min) measurements, this actually corresponding where about 50% of the bubbles initially present have disappeared, i.e., where die optical density reading is about half the initial reading, this being set, in the graph, relative to the height at which the transparency of the pressurized suspension is maximal (base line). This point which is also in the vicinity where the slope of the curve is maximal is defined as the critical pressure PC. It was found that for a given gas, PC does not only depend on the aforementioned parameters but also, and particularly so, on the actual concentration of gas (or gases) already dissolved in the carrier liquid: the higher the gas concentration, the higher the critical pressure. In this connection, one can therefore increase the resistance to collapse under pressure of the microvesicles by making the carrier phase saturated with a soluble gas, the latter being the same, or not, (i.e., a different gas) as the one that fills the vesicles. As an example, air-filled microvesicles could be made very resistant to overpressures (>120 Torr) by using, as a carrier liquid, a saturated solution of $CO_2$. Unfortunately, this finding of limited value in the diagnostic field since once the contrast agent is injected to the bloodstream of patients (the gas content of which is of course outside control), it becomes diluted therein to such an extent that the effect of the gas originally dissolved in the injected sample becomes negligible.

Another readily accessible parameter to reproducibly compare the performance of various gases as microsphere fillers is the width of the pressure interval ($\Delta P$) limited by the pressure values under which the bubble counts (as expressed by the optical densities) is equal to the 75% and 25% of the original bubble count. Now, it has been surprisingly found that for gases where the pressure difference $\Delta P = P_{25} - P_{75}$ exceeds a value of about 25–30 Torr, the killing effect of the blood pressure on the gas-filled microvesicles is minimized, i.e., the actual decrease in the bubble count is sufficiently slow not to impair the significance, accuracy and reproducibility of echographic measurements.

It was found, in addition, that the values of PC and $\Delta P$ also depend on the rate of rising the pressure in the test experiments illustrated by FIG. 1, i.e., in a certain interval of pressure increase rates (e.g., in the range of several tens to several hundreds of Torr/min), the higher the rate, the larger the values for PC and $\Delta P$. For this reason, the comparisons effected under standard temperature conditions were also carried out at the constant increase rate of 100 Torr/min. It should however be noted that this effect of the pressure increase rate on the measure of the PC and $\Delta P$ values levels off for very high rates; for instance the values measured under rates of several hundreds of Torr/min are not significantly different from those measured under conditions ruled by heart beats.

Although the very reasons why certain gases obey the aforementioned properties, while others do not, have not been entirely clarified, it would appear that some relation possibly exists in which, in addition to molecular weight and water solubility, dissolution kinetics, and perhaps other parameters, are involved. However these parameters need not be known to practice the present invention since gas eligibility can be easily determined according to the afore-discussed criteria.

The gaseous species which particularly suit the invention are, for instance, halogenated hydrocarbons like the freons and stable fluorinated chalcogenides like $SF_6$, $SeF_6$ and the like.

It has been mentioned above that the degree of gas saturation of the liquid used as carrier for the microvesicles according to the invention has an importance on the vesicle stability under pressure variations. Indeed, when the carrier liquid in which the microvesicles are dispersed for making the echogenic suspensions of the invention is saturated at equilibrium with a gas, preferably the same gas with which the microvesicles are filled, the resistance of the microvesicles to collapse under variations of pressure is markedly increased. Thus, when the product to be used as a contrast agent is sold dry to be mixed just before use with the carrier liquid (see for instance the products disclosed in PCT/EP91/00620 mentioned hereinbefore), it is quite advantageous to use, for the dispersion, a gas saturated aqueous carrier. Alternatively, when marketing ready-to-use microvesicle suspensions as contrast agents for echography, one will advantageously use as the carrier liquid for the preparation a gas saturated aqueous solution; in this case the storage life of the suspension will be considerably increased and the product may be kept substantially unchanged (no substantial bubble count variation) for extended periods, for instance several weeks to several months, and even over a year in special cases. Saturation of the liquid with a gas may be effected most easily by simply bubbling the gas into the liquid for a period of time at room temperature.

The invention described herein can be further elucidated by the description of the following representative (but not limiting) embodiments, numbered 1–18:

1. A method for imparting resistance against collapsing to contrast agents for ultrasonic echography which consist of gas-filled microvesicles in suspension in aqueous liquid carrier phases, i.e., either microbubbles bounded by an evanescent gas/liquid interfacial closed surface, or microballoons bounded by a material envelope, said collapsing resulting, at least in part, from pressure increases effective, e.g., when the said suspensions are injected into the blood stream of patients, said method comprising forming said microvesicles in the presence of a gas, or if the microvesicles are already made filling them with this gas, which is a physiologically acceptable gas, or gas mixture, at least a fraction of which has a solubility in water expressed in liters of gas by liter of water under standard conditions divided by the square root of the molecular weight in daltons which does not exceed 0.003.

2. The method of embodiment 1, which is carried out in two steps, in the first step the microvesicles or dry precursors thereof are initially prepared under an atmosphere of a first gas, then in the second step at least a fraction of the first gas is substantially substituted by a second gas, the latter being said physiologically acceptable gas.

3. The method of embodiment 1, in which the physiologically acceptable gas used is selected from $SF_6$ or Freon® such as $CF_4$, $CBrF_3$, $C_4F_8$, $CClF_3$, $CCl_2F_2$, $C_2F_6$, $C_2ClF_5$, $CBrClF_2$, $C_2Cl_2F_4$, $CBr_2F_2$ and $C_4F_{10}$.

4. The method of embodiment 2, in which the gas used in the first step is a kind that allows effective control of the average size and concentration of the microvesicles in the carrier liquid, and the physiologically acceptable gas added in the second step ensures prolonged useful echogenic life to the suspension for in vivo ultrasonic imaging.

5. The method of embodiment 1, in which the aqueous phase carrying the microbubbles contains dissolved film-forming surfactants in lamellar or laminar form, said surfactants stabilizing the microbubbles boundary at the gas to liquid interface.

6. The method of embodiment 5, in which said surfactants comprise one or more phospholipids.

7. The method of embodiment 6, in which at least part of the phospholipids are in the form of liposomes.

8. The method of embodiment 6, in which at least one of the phospholipids is a diacylphosphatidyl compound wherein the acyl group is a $C_{16}$ fatty acid residue or a higher homologue thereof.

9. The method of embodiments 1 and 2, in which the microballoon material envelope is made of an organic polymeric membrane.

10. The method of embodiment 9, in which the polymers of the membrane are selected from polylactic or polyglycolic acid and their copolymers, reticulated serum albumin, reticulated haemoglobin, polystyrene, and esters of polyglutamic and polyaspartic acids.

11. The method of embodiment 1, in which the forming of the microvesicles with said physiologically acceptable gas is effected by alternately subjecting dry precursors thereof to reduced pressure and restoring the pressure with said gas, and finally dispersing the precursors in a liquid carrier.

12. The method of embodiment 1, in which the filling of the microballoons with said physiologically acceptable gas is effected by simply flushing the suspension with said gas under ambient pressure.

13. The method of embodiment 1, which comprises making the microvesicles by any standard method known in the art but operating under an atmosphere composed at least in part of said gas.

14. Suspensions of gas filled microvesicles distributed in an aqueous carrier liquid to be used as contrast agents in ultrasonic echography, characterized in that the gas is physiologically acceptable and such that at least a portion thereof has a solubility in water, expressed in liter of gas by liter of water under standard conditions, divided by the square root of the molecular weight which does not exceed 0.003.

15. The aqueous suspensions of embodiment 14, characterized in that the gas is such that the pressure difference $\Delta P$ between those pressures which, when applied under standard conditions and at a rate of about 100 Torr/min to the suspension cause the collapsing of about 75%, respectively 25%, of the microvesicles initially present, is at least 25 Torr.

16. Aqueous suspensions according to embodiment 14, in which the microvesicles are microbubbles filled with said physiologically acceptable gas suspended in an aqueous carrier liquid containing phospholipids whose fatty acid residues contain 16 carbons or more.

17. Contrast agents for echography in precursor form consisting of a dry powder comprising lyophilized liposomes and stabilizers, this powder being dispersible in aqueous liquid carriers to form echogenic suspensions of gas-filled microbubbles, characterized in that it is stored under an atmosphere comprising a physiologically acceptable gas whose solubility in water, expressed in liter of gas by liter of water under standard conditions, divided by the square root of the molecular weight does not exceed 0.003.

18. The contrast agent precursors of embodiment 17, in which the liposomes comprise phospholipids whose fatty acid residues have 16 or more carbon atoms.

The following Examples further illustrate various aspects of the invention.

EXAMPLE 12

Albumin microvesicles filled with air or various gases were prepared as described in EP-A-0324938 using a 10 ml calibrated syringe filled with a 5% human serum albumin (HSA) obtained from the Blood Transfusion Service, Red-Cross Organization, Bern, Switzerland. A sonicator probe (Sonifier Model 250 from Branson Ultrasonic Corp, USA) was lowered into the solution down to the 4 ml mark of the syringe and sonication was effected for 25 sec (energy setting=8). Then the sonicator probe was raised above the solution level up to the 6 ml mark and sonication was resumed under the pulse mode (cycle=0.3) for 40 sec. After standing overnight at 4° C., a top layer containing most of the microvesicles had formed by buoyancy and the bottom layer containing unused albumin debris of denatured protein and other insolubles was discarded. After resuspending the microvesicles in fresh albumin solution the mixture was allowed to settle again at room temperature and the upper layer was finally collected. When the foregoing sequences were carried out under the ambient atmosphere, air filled microballoons were obtained. For obtaining microballoons filled with other gases, the albumin solution was first purged with a new gas, then the foregoing operational sequences were effected under a stream of this gas flowing on the surface of the solution; then at the end of the operations, the suspension was placed in a glass bottle which was extensively purged with the desired gas before sealing.

The various suspensions of microballoons filled with different gases were diluted to 1:10 with distilled water saturated at equilibrium with air, then they were placed in an optical cell as described above and the absorbance was recorded while increasing steadily the pressure over the suspension. During the measurements, the suspensions temperature was kept at 25° C.

The results are shown in the Table 1 below and are expressed in terms of the critical pressure PC values registered for a series of gases defined by names or formulae, the characteristic parameters of such gases, i.e., Mw and water solubility being given, as well as the original bubble count and bubble average size (mean diameter in volume).

TABLE 1

| Sample | Gas | Mw | Solubility | Bubble Count ($10^8$/ml) | Bubble size (μm) | PC (Torr) | S gas √Mw |
|---|---|---|---|---|---|---|---|
| AFre1 | $CF_4$ | 88 | .0038 | 0.8 | 5.1 | 120 | .0004 |
| AFre2 | $CBrF_3$ | 149 | .0045 | 0.1 | 11.1 | 104 | .0004 |
| ASF1 | $SF_6$ | 146 | .005 | 13.9 | 6.2 | 150 | .0004 |
| ASF2 | $SF_6$ | 146 | .005 | 2.0 | 7.9 | 140 | .0004 |
| AN1 | $N_2$ | 28 | .0144 | 0.4 | 7.8 | 62 | .0027 |
| A14 | Air | 29 | .0167 | 3.1 | 11.9 | 53 | .0031 |
| A18 | Air | 29 | .0167 | 3.8 | 9.2 | 52 | — |
| A19 | Air | 29 | .0167 | 1.9 | 9.5 | 51 | — |
| AMe1 | $CH_4$ | 16 | .032 | 0.25 | 8.2 | 34 | .008 |
| AKr1 | Kr | 84 | .059 | 0.02 | 9.2 | 86 | .006 |
| AX1 | Xe | 131 | .108 | 0.06 | 17.2 | 65 | .009 |
| AX2 | Xe | 131 | .108 | 0.03 | 16.5 | 89 | .009 |

From the results of Table 1, it is seen that the critical pressure PC increases for gases of lower solubility and higher molecular weight. It can therefore be expected that microvesicles filled with such gases will provide more durable echogenic signals in vivo. It can also be seen that average bubble size generally increases with gas solubility.

EXAMPLE 13

Aliquots (1 ml) of some of the microballoon suspensions prepared in Example 12 were injected in the Jugular vein of experimental rabbits in order to test echogenicity in vivo. Imaging of the left and right heart ventricles was carried out in the grey scale mode using an Acuson 128-XP5 echography apparatus and a 7.5 MHz transducer. The duration of contrast enhancement in the left ventricle was determined by recording the signal for a period of time. The results are gathered in Table 2 below which also shows the PC of the gases used.

TABLE 2

| Sample (Gas) | Duration of contrast (sec) | PC (Torr) |
|---|---|---|
| AMe1 ($CH_4$) | zero | 34 |
| A14 (air) | 10 | 53 |
| A18 (air) | 11 | 52 |
| AX1 (Xe) | 20 | 65 |
| AX2 (Xe) | 30 | 89 |
| ASF2 ($SF_6$) | >60 | 140 |

From the above results, one can see the existence of a definite correlation between the critical pressure of the gases tried and the persistence in time of the echogenic signal.

EXAMPLE 14

A suspension of echogenic air-filled galactose microparticles (Echovist® from Schering AG) was obtained by shaking for 5 sec 3 g of the solid microparticles in 8.5 ml of a 20% galactose solution. In other preparations, the air above a portion of Echovist® particles was evacuated (0.2 Torr) and replaced by an $SF_6$ atmosphere, whereby, after addition of the 20% galactose solution, a suspension of microparticles containing associated sulfur hexafluoride was obtained. Aliquots (1 ml) of the suspensions were administered to experimental rabbits (by injection in the jugular vein) and imaging of the heart was effected as described in the previous example. In this case the echogenic microparticles do not transit through the lung capillaries, hence imaging is restricted to the right ventricle and the overall signal persistence has no particular significance. The results of Table 3 below show the value of signal peak intensity a few seconds after injection.

TABLE 3

| Sample No | Gas | Signal peak (arbitrary units) |
|---|---|---|
| Gal1 | air | 114 |
| Gal2 | air | 108 |
| Gal3 | $SF_6$ | 131 |
| Gal4 | $SF_6$ | 140 |

It can be seen that sulfur hexafluoride, an inert gas with low water solubility, provides echogenic suspensions which generate echogenic signals stronger than comparable suspensions filled with air. These results are particularly interesting in view of the teachings of EP-A-0441468 and EP-A-0357163 (Schering) which disclose the use for echography purposes of microparticles, respectively, cavitate and clathrate compounds filled with various gases including $SF_6$; these documents do not however report particular advantages of $SF_6$ over other more common gases with regard to the echogenic response.

EXAMPLE 15

A series of echogenic suspensions of gas-filled microbubbles were prepared by the general method set forth below:

One gram of a mixture of hydrogenated soya lecithin (from Nattermann Phospholipids GmbH, Germany) and dicetyl-phosphate (DCP), in 9/1 molar ratio, was dissolved in 50 ml of chloroform, and the solution was placed in a 100 ml round flask and evaporated to dryness on a Rotavapor apparatus. Then, 20 ml of distilled water were added and the mixture was slowly agitated at 75° C. for an hour. This resulted in the formation of a suspension of multilamellar liposomes (MLV) which was thereafter extruded at 75° C. through, successively, 3 μm and 0.8 μm polycarbonate membranes (Nuclepore(D)). After cooling, 1 ml aliquots of the extruded suspension were diluted with 9 ml of a concentrated lactose solution (83 g/l), and the diluted suspensions were frozen at −45° C. The frozen samples were thereafter freeze-dried under high vacuum to a free-flowing powder in a vessel which was ultimately filled with air or a gas taken from a selection of gases as indicated in Table 4 below. The powdery samples were then resuspended in 10 ml of water as the carrier liquid, this being effected under a stream of the same gas used to fill the said vessels. Suspension was effected by vigorously shaking for 1 min on a vortex mixer.

The various suspensions were diluted 1:20 with distilled water equilibrated beforehand with air at 25° C. and the dilutions were then pressure tested at 25° C. as disclosed in Example 12 by measuring the optical density in a spectrophotometric cell which was subjected to a progressively increasing hydrostatic pressure until all bubbles had collapsed. The results are collected in Table 4 below which, in addition to the critical pressure PC, gives also the ΔP values (see FIG. 1).

TABLE 4

| Sample No | Gas | Mw | Solubility in $H_2O$ | Bubble Count ($10^8$/ml) | PC (Torr) | increment Δ P (Torr) |
|---|---|---|---|---|---|---|
| LFre1 | $CF_4$ | 88 | .0038 | 1.2 | 97 | 35 |
| LFre2 | $CBrF_3$ | 149 | .0045 | 0.9 | 116 | 64 |
| LSF1 | $SF_6$ | 146 | .005 | 1.2 | 92 | 58 |
| LFre3 | $C_4F_8$ | 200 | .016 | 1.5 | 136 | 145 |
| L1 | air | 29 | .0167 | 15.5 | 68 | 17 |
| L2 | air | 29 | .0167 | 11.2 | 63 | 17 |
| LAr1 | Ar | 40 | .031 | 14.5 | 71 | 18 |
| LKr1 | Kr | 84 | .059 | 12.2 | 86 | 18 |
| LXe1 | Xe | 131 | .108 | 10.1 | 92 | 23 |
| LFre4 | $CHClF_2$ | 86 | .78 | — | 83 | 25 |

The foregoing results clearly indicate that the highest resistance to pressure increases is provided by the most water-insoluble gases. The behavior of the microbubbles is therefore similar to that of the microballoons in this regard. Also, the less water-soluble gases with the higher molecular weights provide the flattest bubble-collapse/pressure curves (i.e., ΔP is the widest) which is also an important factor of echogenic response durability in vivo, as indicated hereinbefore.

EXAMPLE 16

Some of the microbubble suspensions of Example 15 were injected to the jugular vein of experimental rabbits as indicated in Example 13 and imaging of the left heart ventricle was effected as indicated previously. The duration of the period for which a useful echogenic signal was detected was recorded and the results are shown in Table 5 below in which $C_4F_8$ indicates octafluorocyclobutane.

TABLE 5

| Sample No | Type of gas | Contrast duration (sec) |
|---|---|---|
| L1 | Air | 38 |
| L2 | Air | 29 |
| LMe1 | $CH_4$ | 47 |
| LKr1 | Krypton | 37 |
| LFre1 | $CF_4$ | >120 |
| LFre2 | $CBrF_3$ | 92 |
| LSF1 | $SF_6$ | >112 |
| LFre3 | $C_4F_8$ | >120 |

These results indicate that, again in the case of microbubbles, the gases according to the criteria of the present invention will provide ultrasonic echo signal for a much longer period than most gases used until now.

EXAMPLE 17

Suspensions of microbubbles were prepared using different gases exactly as described in Example 15, but replacing the lecithin phospholipid ingredient by a mole equivalent of diarachidoylphosphatidylcholine ($C_{20}$ fatty acid residue) available from Avanti Polar Lipids, Birmingham, Ala. USA. The phospholipid to DCP molar ratio was still 9/1. Then the suspensions were pressure tested as in Example 15; the results, collected in Table 6A below, are to be compared with those of Table 4.

TABLE 6A

| Sample No | Type of Gas | Mw of Gas | Solubility in water | Bubble Count ($10^8$/ml) | PC (Torr) | increment Δ P (Torr) |
|---|---|---|---|---|---|---|
| LFre1 | $CF_4$ | 88 | .0038 | 3.4 | 251 | 124 |
| LFre2 | $CBrF_3$ | 149 | .0045 | 0.7 | 121 | 74 |
| LSF1 | $SF_6$ | 146 | .005 | 3.1 | 347 | >150 |
| LFre3 | $C_4F_8$ | 200 | .016 | 1.7 | >350 | >200 |
| L1 | Air | 29 | .0167 | 3.8 | 60 | 22 |
| LBu1 | Butane | 58 | .027 | 0.4 | 64 | 26 |
| LAr1 | Argon | 40 | .031 | 3.3 | 84 | 47 |
| LMe1 | $CH_4$ | 16 | .032 | 3.0 | 51 | 19 |
| LEt1 | $C_2H_6$ | 44 | .034 | 1.4 | 61 | 26 |
| LKr1 | Kr | 84 | .059 | 2.7 | 63 | 18 |
| LXe1 | Xe | 131 | .108 | 1.4 | 60 | 28 |
| LFre4 | $CHClF_2$ | 86 | .78 | 0.4 | 58 | 28 |

The above results, compared to that of Table 4, show that, at least with low solubility gases, by lengthening the chain of the phospholipid fatty acid residues, one can dramatically increase the stability of the echogenic suspension toward pressure increases. This was further confirmed by repeating the foregoing experiments but replacing the phospholipid component by its higher homolog, i.e., di-behenoylphosphatidylcholine ($C_{22}$ fatty acid residue). In this case, the resistance to collapse with pressure of the microbubbles suspensions was still further increased.

Some of the microbubbles suspensions of this Example were tested in dogs as described previously for rabbits (imaging of the heart ventricles after injection of 5 ml samples in the anterior cephalic vein). A significant enhancement of the useful in vivo echogenic response was noted, in comparison with the behavior of the preparations disclosed in Example 15, i.e., the increase in chain length of the fatty-acid residue in the phospholipid component increases the useful life of the echogenic agent in vivo.

In the next Table below, there is shown the relative stability in the left ventricle of the rabbit of microbubbles ($SF_6$) prepared from suspensions of a series of phospholipids whose fatty acid residues have different chain lengths (<injected dose: 1 ml/rabbit).

TABLE 6B

| Phospholipid | Chain length ($C_n$) | PC (Torr) | increment Δ P (Torr) | Duration of contrast (sec) |
|---|---|---|---|---|
| DMPC | 14 | 57 | 37 | 31 |
| DPPC | 16 | 100 | 76 | 105 |
| DSPC | 18 | 115 | 95 | 120 |
| DAPC | 20 | 266 | 190 | >300 |

It has been mentioned hereinabove that for the measurement of resistance to pressure described in these Examples, a constant rate of pressure rise of 100 Torr/min was maintained. This is justified by the results given below which show the variations of the PC values for different gases in function to the rate of pressure increase. In these samples DMPC was the phospholipid used.

| Gas | PC (Torr) Rate of pressure increase (Torr/min) | | |
|---|---|---|---|
| Sample | 40 | 100 | 200 |
| $SF_6$ | 51 | 57 | 82 |
| Air | 39 | 50 | 62 |
| $CH_4$ | 47 | 61 | 69 |
| Xe | 38 | 43 | 51 |
| Freon 22 | 37 | 54 | 67 |

EXAMPLE 18

A series of albumin microballoons as suspensions in water were prepared under air in a controlled sphere size fashion using the directions given in Example 12. Then the air in some of the samples was replaced by other gases by the gas-exchange sweep method at ambient pressure. Then, after diluting to 1:10 with distilled water as usual, the samples were subjected to pressure testing as in Example 12. From the results gathered in Table 7 below, it can be seen that the two-steps preparation mode gives, in some cases, echo-generating agents with better resistance to pressure than the one-step preparation mode of Example 12.

TABLE 7

| Sample No | Type of gas | Mw of the gas | Solubility in water | Initial Bubble Count ($10^8$/ml) | PC (Torr) |
|---|---|---|---|---|---|
| A14 | Air | 29 | .0167 | 3.1 | 53 |
| A18 | Air | 29 | .0167 | 3.8 | 52 |
| A18/$SF_6$ | $SF_6$ | 146 | .005 | 0.8 | 115 |
| A18/$C_2H_6$ | $C_2H_6$ | 30 | .042 | 3.4 | 72 |
| A19 | Air | 29 | .0167 | 1.9 | 51 |
| A19/$SF_6$ | $SF_6$ | 146 | .005 | 0.6 | 140 |
| A19/Xe | Xe | 131 | .108 | 1.3 | 67 |
| A22/$CF_4$ | $CF_4$ | 88 | .0038 | 1.0 | 167 |
| A22/Kr | Kr | 84 | .059 | 0.6 | 85 |

EXAMPLE 19

The method of the present invention was applied to an experiment as disclosed in the prior art, for instance Example 1 WO-92/11873. Three grams of Pluronic® F68 (a copolymer of polyoxyethylene-polyoxypropylene with a molecular weight of 8400), 1 g of dipalmitoylphosphatidylglycerol (Na salt, Avanti Polar Lipids) and 3.6 g of glycerol were added to 80 ml of distilled water. After heating at about 80° C., a clear homogenous solution was obtained. The tenside solution was cooled to room temperature and the volume was adjusted to 100 ml. In some experiments (see Table 8) dipalmitoylphosphatidylglycerol was replaced by a mixture of diarachidoylphosphatldylcholine (920 mg) and 80 mg of dipalmitoylphosphatidic acid (Na salt, Avanti Polar lipids).

The bubble suspensions were obtained by using two syringes connected via a three-way valve. One of the syringes was filled with 5 ml of the tenside solution while the other was filled with 0.5 ml of air or gas. The three-way valve was filled with the tenside solution before it was connected to the gas-containing syringe. By alternatively operating the two pistons, the tenside solutions were transferred back and forth between the two syringes (5 times in each direction), milky suspensions were formed. After dilution (1:10 to 1:50) with distilled water saturated at equilibrium with air, the resistance to pressure of the preparations was determined according to Example 12, the pressure increase rate was 240 Torr/min. The following results were obtained:

TABLE 8

| Phospholipid | Gas | Pc (mm Hg) | DP (mm Hg) |
|---|---|---|---|
| DPPG | air | 28 | 17 |
| DPPG | $SF_6$ | 138 | 134 |
| DAPC/DPPA 9/1 | air | 46 | 30 |
| DAPC/DPPA 9/1 | $SF_6$ | 269 | 253 |

It follows that by using the method of the invention and replacing air with other gases, e.g., $SF_6$, even with known preparations a considerable improvements, i.e., increase in the resistance to pressure, may be achieved. This is true both in the case of negatively charged phospholipids (e.g., DPPG) and in the case of mixtures of neutral and negatively charged phospholipids (DAPC/DPPA).

The above experiment further demonstrates that the recognized problem sensitivity of microbubbles and microballoons to collapse when exposed to pressure, i.e., when suspensions are injected into living beings, has advantageously been solved by the method of the invention. Suspensions with microbubbles or microballoons with greater resistance against collapse and greater stability can advantageously be produced providing suspensions with better reproducibility and improved safety of echographic measurements performed in vivo on a human or animal body.

Further Methods of the Invention and Gas Mixtures Used therein

Agents used for imaging of the left heart and myocardium should provide clear images and should have good resistance to pressure variation but should not be overlasting and should not disturb images created immediately upon injection. Recirculation is not a desirable feature of agents whose intended use is to cover a range of applications and clear imaging. Obviously, it is highly desirable to modulate the pressure resistance or persistence of the contrast agent after injection, i.e., to use suspensions of bubbles (or microballoons) designed with sufficient pressure resistance but with controlled life-time in the circulation. This demand is fulfilled by the invention using the gas mixtures described below.

Briefly summarized, the invention relates to an injectable ultrasound contrast medium in the form of microbubbles or microballoons comprising at least two biocompatible, at the body temperature gaseous, substances A and B forming a mixture which when in suspension with usual surfactants, additives and stabilizers provides useful ultrasound contrast agents. At least one of the components (B) in the mixture is a gas whose molecular weight is above 80 daltons and whose solubility in water is below 0.0283 ml of gas per ml of water under standard conditions. Gas solubilities referred to below correspond to the Bunsen coefficients and the molecular weights above 80 daltons are considered as relatively high, while the molecular weights below 80 daltons are considered as relatively low. The mixtures of the invention therefore may be defined as mixtures of in which the major portion of the mixture is comprised of "a relatively low" molecular weight gas or gases, while the minor portion of the mixture is comprised of "a relatively high" molecular weight gas or gas mixture. The quantity of this "minor" or activating component (B) in the contrast medium is practically always between 0.5 and 41 volume percent. The other component (A) of the ultrasound contrast media may be a gas or a mixture of gases whose solubility in water is above that of nitrogen (0.0144 ml/ml of water under standard conditions) and whose quantity in the mixture is practically always in a proportion of between 59–99.5% by vol. This "major" or dominating component is preferably a gas or gases whose molecular weights are relatively low, usually below 80 daltons, and is chosen from gases such as oxygen, air, nitrogen, carbon dioxide or mixtures thereof.

In the ultrasound contrast medium of the invention the gas whose molecular weight is above 80 daltons may be a mixture of gases or mixture of substances which are gaseous at body temperature but which, at ambient temperatures, may be in the liquid state. Such gaseous or liquid substances may be useful in the contrast media of the invention as long as the molecular weight of each such substance is greater than 80 daltons and the solubility in water of each substance is below 0.0283 ml of gas per ml of water under standard conditions.

When filled with the contrast media of the invention and dispersed in an aqueous carrier containing usual surfactants, additives and stabilizers, the microbubbles formed provide an injectable contrast agent for ultrasonic imaging, of controlled resistance to pressure variations and modulated persistence after injection. In addition to the microbubbles, the contrast agent of the invention will contain surfactants stabilizing the microbubble evanescent gas/liquid envelope, and optionally, hydrophilic agents and other additives. The additives may include block copolymers of polyoxypropylene and polyoxyethylene (poloxamers), polyoxyethylenesorbitans, sorbitol, glycerol-polyalkylene stearate, glycerolpolyoxyethylene ricinoleate, homo- and copolymers of polyalkylene glycols, soybean-oil as well as hydrogenated derivatives, ethers and esters of sucrose or other carbohydrates with fatty acids, fatty alcohols, glycerides of soya-oil, dextran, sucrose and carbohydrates. Surfactants may be film forming and non-film forming and may include polymerizable amphiphilic compounds of the type of linoleyl-lecithins or polyethylene dodecanoate. Preferably, the surfactants comprise one or more film forming surfactants in lamellar or laminar form selected between phosphatidic acid, phosphatidylcholine, phosphatidylethanolamine, phosphatidylserine, phosphatidylglycerol, phosphatidylinositol, cardiolipin, sphingomyelin and mixtures thereof.

The invention also comprises a method of making the ultrasound contrast agents by suspending in a physiologically acceptable carrier containing usual surfactants and stabilizers, gas filled microbubbles or microballoons comprising a mixture of gases at least one of which is a gas whose minimum effective amount in the mixture may be determined according to the expression:

$$B_c \% = K/e^{bM_{wt}} + C$$

in which $B_c$ % (by vol.) is the total quantity of the component B in the mixture, K, C & b are constants with values of 140, −10.8 and 0.012 respectively, $M_{wt}$ represents the molecular weight of the component B exceeding 80. The contrast agents made according to the present method comprise suspensions of microbubbles or microballoons with excellent resistance to pressure variations and a controlled resorption rate.

The invention also includes a kit comprising a dry formulation which is usually stored under a mixture of gases and/or liquids that are converted into gases at body temperature. When dispersed in a physiologically acceptable carrier liquid, the dry formulation with the mixture of gases and/or liquids produces the ultrasound contrast agent of the invention. A method of storage of the dry lyophilised formulation in the presence of the ultrasound contrast media is also disclosed.

The invention further comprises a method of making contrast agents with microbubbles containing the ultrasound contrast media, as well as their use in imaging of organs in human or animal body.

Figure 2:
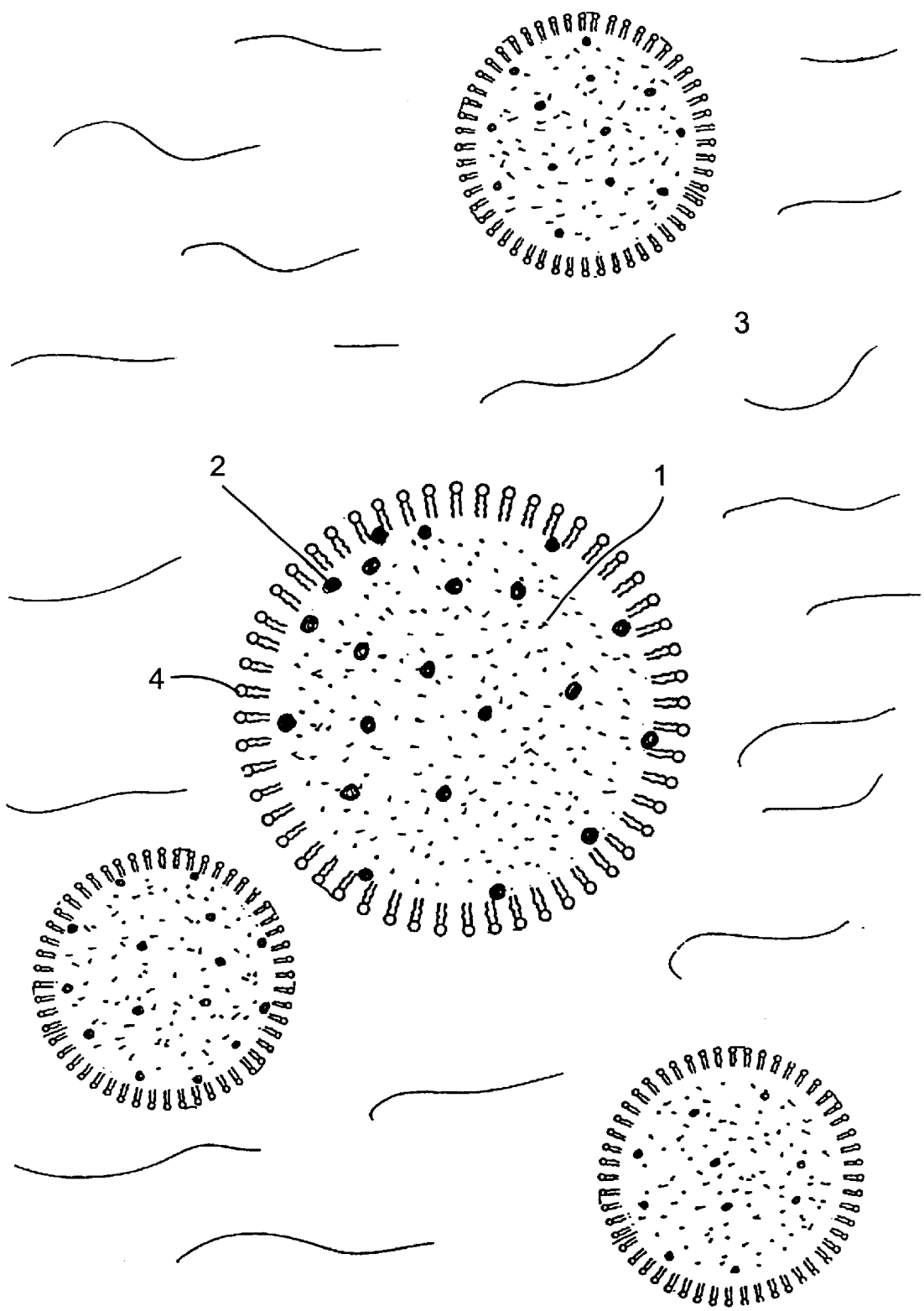
FIG. 2 is a schematic presentation of an ultrasound contrast medium according to the invention.

FIG. 2 is a schematic presentation of an ultrasound contrast medium according to the invention.

Figure 3:
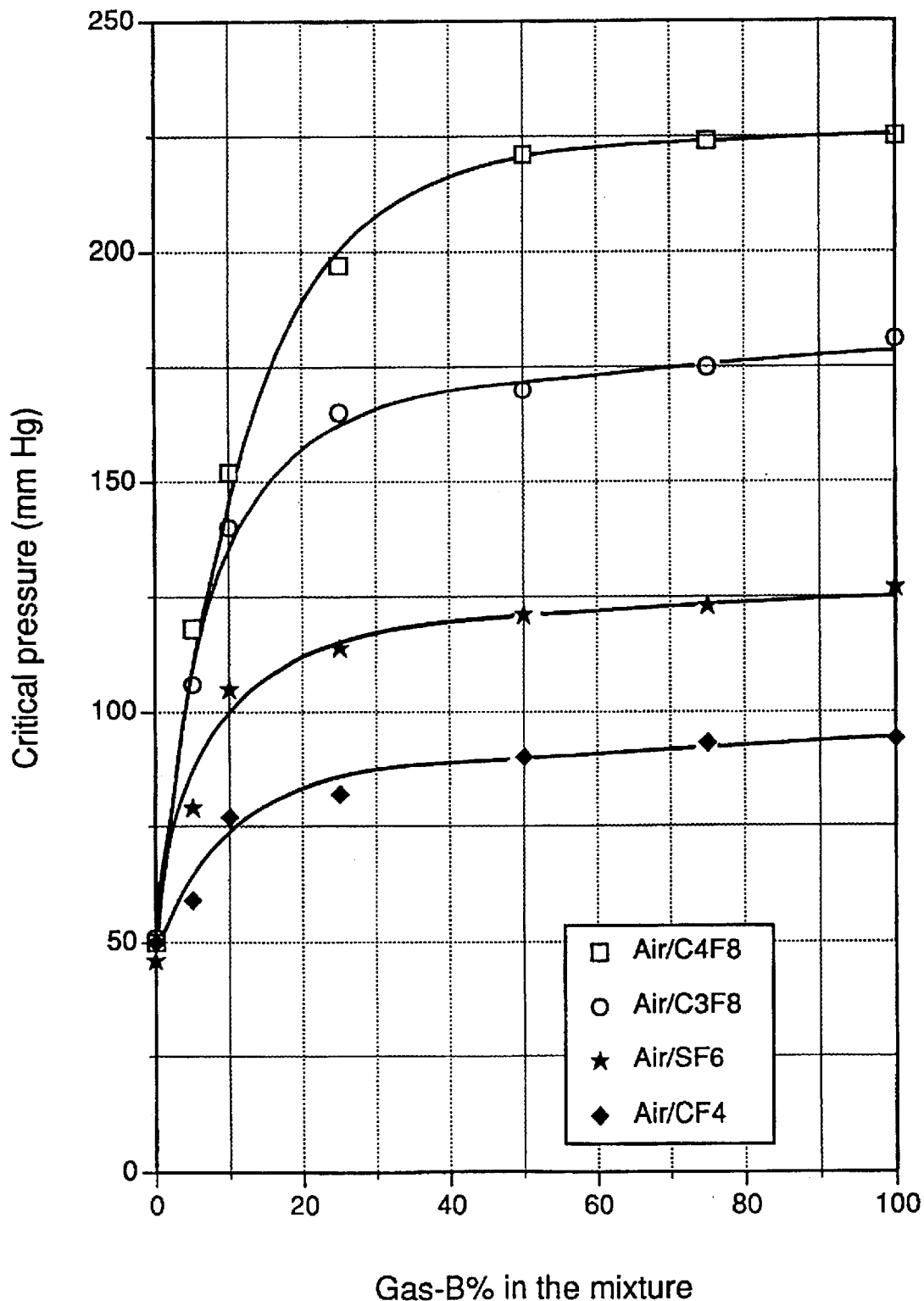
FIG. 3 is schematic diagram of the critical pressure (Pc) of the contrast medium as a function of the quantity of a chosen gas in the mixture.

FIG. 3 is schematic diagram of the critical pressure (Pc) of the contrast medium as a function of the quantity of a chosen gas in the mixture.

Figure 4:
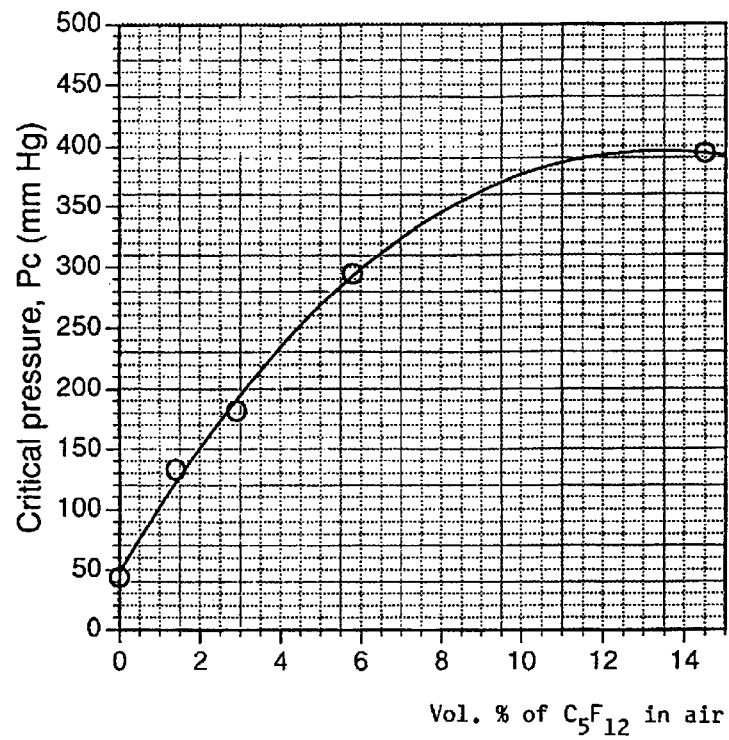
FIG. 4 represents a diagram of the critical pressure (Pc) of a contrast medium made with octafluorocyclobutane ($C_4F_8$) and dodecafluoropentane ($C_5F_{12}$) as a function of quantity of gas in the mixture.
Figure 4:
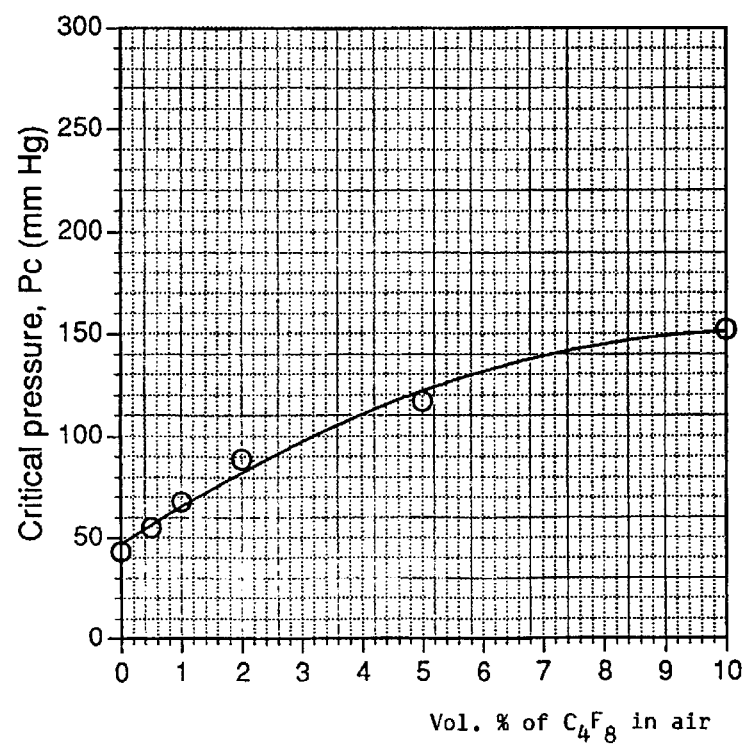

FIG. 4 represents a diagram of the critical pressure (Pc) of a contrast medium made with octafluorocyclobutane ($C_4F_8$) and dodecafluoropentane ($C_5F_{12}$) as a function of quantity of gas in the mixture.

Figure 5:
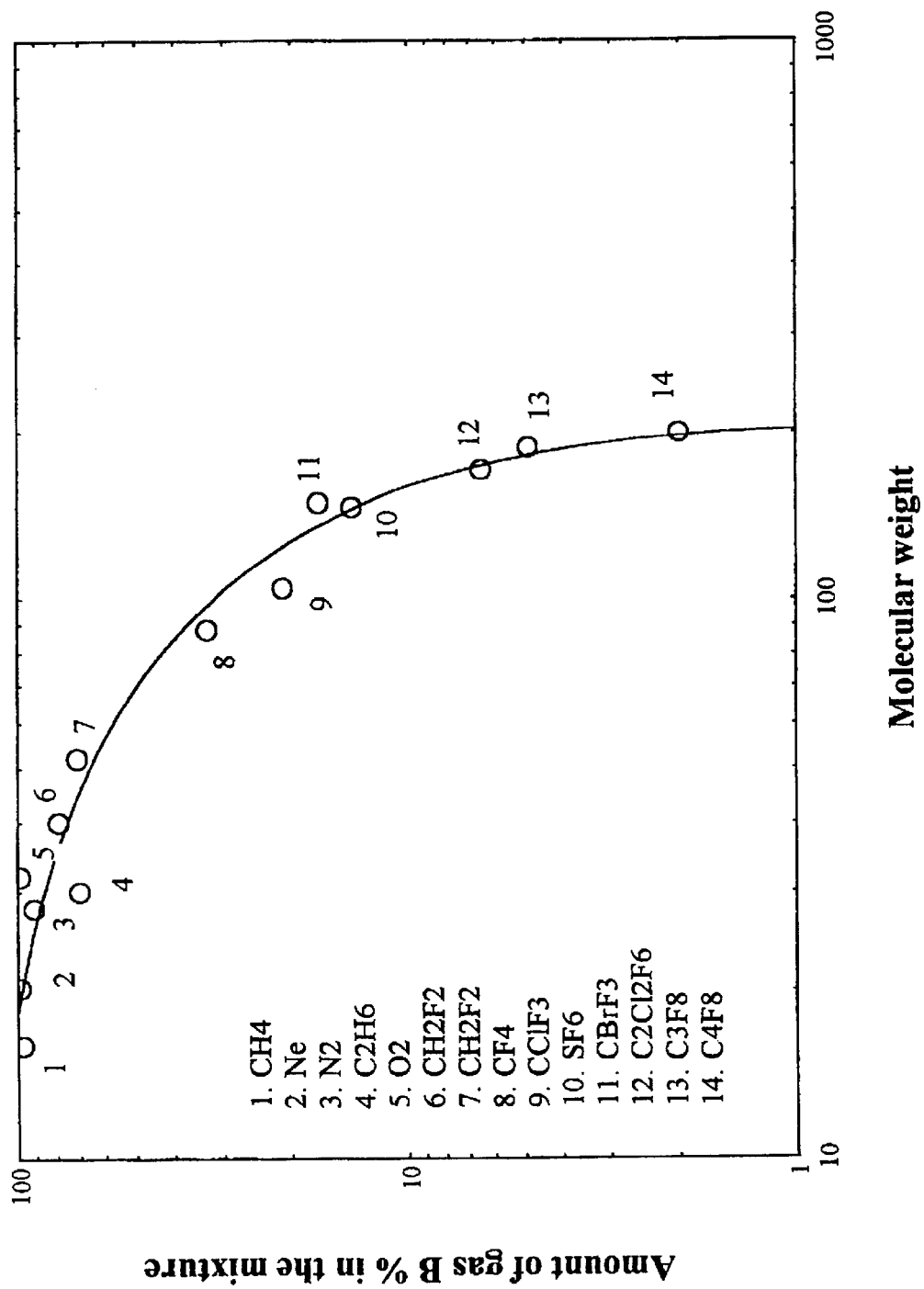
FIG. 5 is a diagram of the minimum amount of a gas in the mixture as a function of the molecular weight.

FIG. 5 is a diagram of the minimum amount of a gas in the mixture as a function of the molecular weight.

Figure 6:
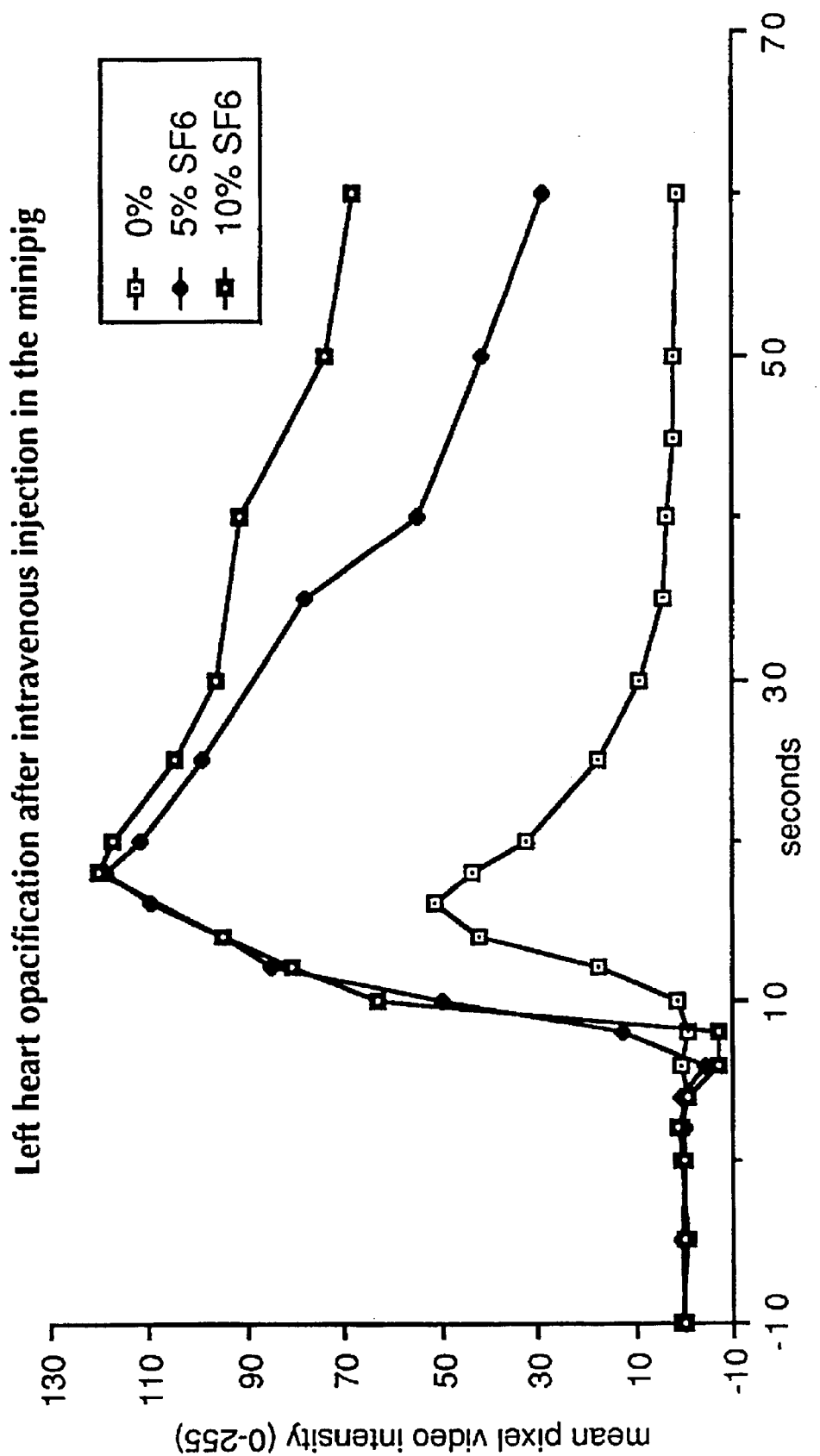
FIG. 6 is a graphic representation of the in vivo echographic response obtained as a function of time in the left ventricle of a minipig after intravenous injection of contrast media containing various concentrations of $SF_6$.

FIG. 6 is a graphic representation of the in vivo echographic responses obtained as a function of time in the left ventricle of a minipig after intravenous injection of contrast media containing various concentrations of $SF_6$.

Figure 7:
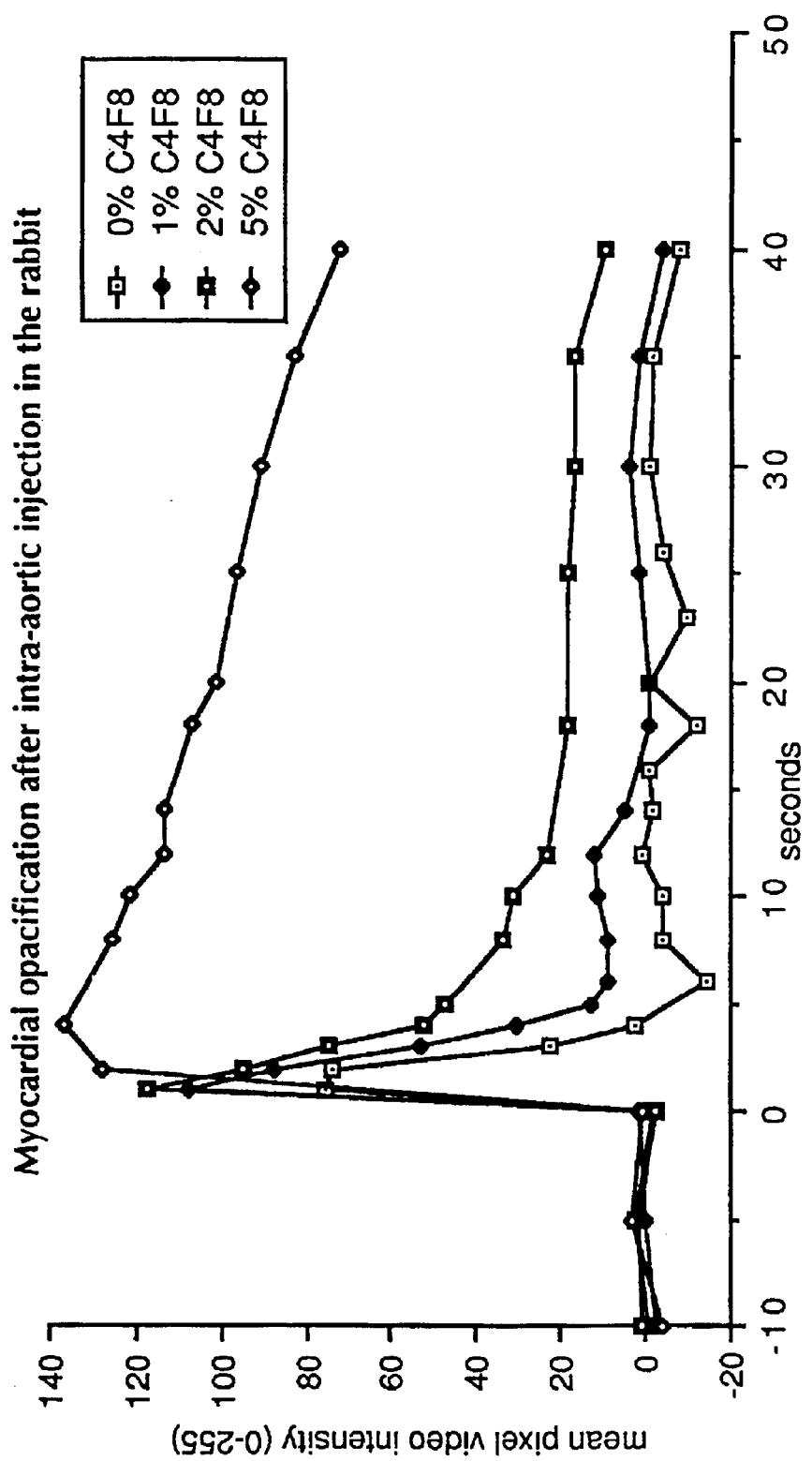
FIG. 7 represents a diagram of in vivo echographic response obtained as a function of time with contrast media containing various concentrations of $C_4F_8$.

FIG. 7 represents a diagram of in vivo echographic response obtained as a function of time with contrast media containing various concentrations of $C_4F_8$.

This invention is based on the unexpected finding that an ultrasound contrast medium comprising bubbles filled with a mixture of at least two biocompatible gaseous or at body temperature gaseous substances A (major or a relatively low molecular weight) and B (activating or a relatively high molecular weight), will provide, in suspension with usual surfactants, additives and stabilizers, injectable ultrasound contrast agents that combine desirable resistance to pressure and a shorter life time in the circulation, both of these parameters being controllable at will. As long as at least one of the (activating) substances or components in the mixture with molecular weight greater than 80 daltons (relatively high molecular weight) is present in certain minimal proportion and as long as its solubility in water is below 0.0283 ml of gas per ml of water at standard conditions, the ultrasound contrast medium will provide echographic properties as good as that obtained when using the pure substances alone. By "activating" it is meant the substance or component which imparts its physical properties to the other components in the mixture rendering the mixture, in terms of echogenicity and resistance to pressure variations, behave the same or almost the same as the substance or component alone (in pure form). The quantity of the first, activating or high molecular weight, component in the contrast medium in most cases vary from as low as 0.5 volume percent (for substances with high molecular weight and low solubility in water) to 41 volume percent. The experiments have shown that substances with the molecular weight below 80 daltons ("low molecular weight") are not suitable as the activating components and that the upper limit of the molecular weight is difficult to establish as all compounds tested were effective as long as their molecular weight was relatively high, i.e., above 80. Thus compounds with the molecular weight of about 240 daltons such as decafluorobutane or 290 daltons such as perfluoropentane have been found as effective activating component. Also there are indications that substances such as 1,2,3-nonadecane tricarboxylic acid, 2-hydroxy-trimethylester with the molecular weight sightly over 500 daltons may also be used as an activating, high molecular weight, component. The other "major" component is correspondingly present in an amount of 59 to 99.5% by volume and may be a gas or gases whose solubility in water is greater than that of nitrogen (0.0144 ml/ml of water under standard conditions). The second component is preferably oxygen, air, nitrogen, carbon dioxide or mixtures thereof and more preferably oxygen or air. However, for the component A, other less common gases like argon, xenon, krypton, $CHClF_2$ or nitrous oxide may also be used. Some of these less common gases may have molecular weights higher than that of $O_2$, $N_2$, air, $CO_2$, etc., for instance above 80 daltons but, in this case, their solubility in water will exceed that of the gases of category B, i.e., will be above 0.0283 ml/ml of water.

It was quite unexpected to find that suspending in an aqueous carrier a mixture formed of as little as 0.5% by volume of a substance such as dodecafluoropentane, or 0.8% by volume of decafluorobutane in admixture with air will produce microbubbles giving excellent echographic images in vivo and resistance to pressure variations. This is particularly surprising since it was heretofore considered necessary that in order to obtain good echographic images of the left heart and the myocardium, these substances, and for that matter a number of others, be used at 100% concentrations, i.e., in pure form (without air). Experiments with mixtures containing different amounts of these, low water solubility, substances and air have shown that the echographic images are as good as those obtained under similar conditions using echographic agents made with only pure substances.

Early studies have shown that rapid elimination of air microbubbles in the circulation takes place because this otherwise physiologically preferred gas is quickly resorbed by dilution and that evanescence of the microbubbles may be reduced through the use of various surfactants, additives and stabilizers. In the early days of development, as a cure to the evanescence problem, microballoons or microvesicles with a material wall have also been proposed. Microvesicles with walls made from natural or synthetic polymers such as lipid bilayers (liposomes) or denatured proteins like albumin filled with air or $CO_2$ have been proposed. The poor resistance to pressure variations and the consequent loss of echogenicity of the older contrast agents has inspired a search for gaseous particles with greater resistance to the pressure variations occurring in the blood stream. Hence, filler gases such as sulfur hexafluoride of more recently dodecafluoropentane have been proposed. Experimentation with these gases have indicated that upon injection, the suspensions of microbubbles made with these gases taken alone are indeed very resistant to collapse in the blood circulation. As a result of these initial findings, close to 200 different gases have been identified as potentially useful for making ultrasound contrast agents. It has thus been unexpectedly found that by mixing oxygen or air with some of these gases resistant to pressure one may obtain ultrasound agents which will have physiologically better tolerance and/or shorter resorption half-life than pure sulfur hexafluoride or dodecafluoropentane, still retaining the good pressure resistance of these gases when taken alone. It is postulated that such surprising behavior of the ultrasound medium of the invention comes from the fact that in the microbubbles containing the gas mixtures diffusion of air into surrounding liquid is slowed by the presence of the large molecules of gas or gases whose solubilities in water are about the same or lower than that of air or oxygen. Although the reasons for this surprising behavior are yet unexplained, it can be postulated that the molecules of the high molecular weight gas, even though in very minor amount, do actually "plug the holes" in the microbubbles boundary and thus prevent escape of the low molecular weight gas by transmembrane diffusion. A graphical presentation of this model is shown in the FIG. 2 where the microbubble containing air (1) admixed with a gas whose molecular weight is above 80 daltons (2) is suspended in an aqueous medium (3). The evanescent outer layer (4) stabilized by a surfactant (e.g., phospholipid) keeps the gas mixture within contained volume defining the microbubble. The activating or minority gas B being uniformly dispersed through out the microbubble volume will have a slower diffusion and ultimately will block the pores of, in the aqueous solution spontaneously formed surfactant membrane-like envelope, thus preventing rapid departure of the smaller and typically more soluble majority component A. On the other hand, the activating or minor component gas (B) exhibit greater affinity for the lipophilic part of the surfactant used for stabilization of the evanescent envelope than oxygen or air. Thus according to another hypothesis these gases tend to concentrate in the vicinity of the membrane preventing or slowing diffusion of the smaller gas(es) across the membrane. Be that as it may, the experimental data gathered suggest that for preparation of echographic media of the invention, the required amount of the activating gas in the mixture is that which corresponds to blocking the porosity of the given membrane material or to the amount required for a monomolecular layer formed on the inner wall of the microbubbles. Therefore, the minimum amount required is that which is needed to block the pores or cover the inner wall of the membrane to prevent escape and resorption of the low molecular weight component.

It is also believed that the superior properties of the ultrasound contrast medium of the invention comes from the combined use of nitrogen, carbon dioxide, oxygen or air (essentially an oxygen/nitrogen mixture) with other gases. Functionally, these biologically and physiologically compatible gases provide important characteristics of the media in question thus ensuring their advantageous properties. Although, the ultrasound contrast media of the invention may be made with a number of other gases serving as the majority or component A, oxygen and air are preferred. In the context of this document air is treated as a "one component" gas.

According to the invention, ultrasound contrast media with high resistance to pressure variations combined with relatively rapid resorption, i.e., clearance in the body can be obtained when using a gas or gases whose molecular weights is/are above 80 daltons in admixture with gas or gases whose solubilities in water are greater than 0.0144 ml/ml of water and molecular weight(s) is/are usually below 80 daltons. Gases such as oxygen or air mixed with substances which are gases at the body temperature but which at the ambient temperatures may be in the liquid state will produce echographic media that will possess all advantages of the gases in the mixture. In other words these mixtures when injected as suspensions of microbubbles will provide clear and crisp images with sharp contrasts (typical for microbubbles with good resistance to pressure variations) and at the same time will be resorbed substantially as easily as if filled with air or oxygen only. Thus by combining air, nitrogen, carbon dioxide or oxygen with a certain controlled amount of any of the known biocompatible high molecular weight substances which at the body temperature are gases, ultrasound contrast media with important and totally unexpected advantages are obtained. As explained above, these media provide the best of each components, i.e., a good resistance to pressure variations from one and a relatively rapid resorption from the other and at the same time eliminating respective disadvantages of each component taken alone in the media. This is particularly surprising as one would have expected properties averaging those of the components taken separately.

As long as the molecular weight of such biocompatible substances (B) is greater than 80 daltons and their solubility in water is below 0.0283 ml of gas per ml of water under standard conditions, such substances in the gaseous or liquid state are useful for the contrast media of the invention. Although in conjunction with suitable surfactants and stabilizers, gases like sulfur hexafluoride, tetrafluoromethane, chlorotrifluoromethane, dichlorodifluoro-methane, bromotrifluoromethane, bromochlorodifluoromethane, dibromo-difluoromethane dichlorotetrafluoroethane, chloropentafluoroethane, hexafluoroethane, hexafluoropropylene, octafluoropropane, hexafluoro-butadiene, octafluoro-2-butene, octafluorocyclobutane, decafluorobutane, perfluorocyclopentane, dodecafluoropentane and more preferably sulfur hexafluoride and/or octafluorocyclobutane, may be used in category B, the media of the invention preferably contains as gas B a gas selected from sulfur hexafluoride, tetrafluoromethane, hexafluoroethane, hexafluoro-propylene, octafluoropropane, hexafluorobutadiene, octafluoro-2-butene, octafluorocyclobutane, decafluorobutane, perfluorocyclopentane, dodecafluoropentane and more preferably sulfur hexafluoride and/or octafluorocyclobutane.

Another unexpected and surprising feature of the invention is the fact that when the criteria of WO 93/05819 are applied to the media of the present invention the Q coefficient obtained with the present gas mixtures is below 5. This is astounding since, according to WO 93/05819 media with Q coefficients below 5 are to be excluded from gases suitable for preparing useful ultrasound contrast media. Nevertheless, it has been found that the uniform gas mixtures of the present invention although having a Q coefficient well below 5, still provide contrast agents useful for ultrasound imaging.

When filled with the contrast media of the invention and dispersed in an aqueous carrier containing usual surfactants, additives and stabilizers, the microbubbles formed provide a useful contrast agent for ultrasonic imaging. In addition to the microbubbles, the contrast agent of the invention will contain surfactants additives and stabilizers. Surfactants which may include one or more film forming surfactants in lamellar or laminar form are used to stabilize the microbubble evanescent gas/liquid envelope. Hydrating agents and/or hydrophilic stabilizer compounds such as polyethylene glycol, carbohydrates such as lactose or sucrose, dextran, starch, and other polysaccharides or other conventional additives like polyoxypropylene glycol and polyoxyethylene glycol; ethers of fatty alcohols with polyoxyalkylene glycols; esters of fatty acids with polyoxyalkylated sorbitan; soaps; glycerol-polyalkylene stearate; glycerol-polyoxyethylene ricinoleate; homo- and copolymers of polyalkylene glycols; polyethoxylated soya-oil and castor oil as well as hydrogenated derivatives; ethers and esters of sucrose or other carbohydrates with fatty acids, fatty alcohols, these being optionally polyoxyakylated; mono-, di- and triglycerides of saturated or unsaturated fatty acids; glycerides of soya-oil and sucrose may also be used. Surfactants may be film forming and non-film forming and may include polymerizable amphiphilic compounds of the type of linoleyl-lecithins or polyethylene dodecanoate. Preferably, the surfactants are film forming and more preferably are phospholipids selected from phosphatidic acid, phosphatidylcholine, phosphatidylethanolamine, phosphatidylserine, phosphatidylglycerol, phosphatidylinositol, cardiolipin, sphingomyelin and mixtures thereof.

It is understood that the invention is not limited to the contrast agents in which only microbubbles are used as carriers of the ultrasound contrast media of the invention. Any suitable particle filled with the ultrasound contrast medium, e.g., liposomes or microballoons having an envelope produced from synthetic or natural polymers or proteins may conveniently be used. Thus it has been established that microballoons prepared with albumin, or liposome vesicles or iodipamide ethyl ester porous particles when filled with the ultrasound contrast media of the invention, provide good echographic contrast agents. Suspensions in which the microbubbles were stabilized with sorbitol or non-ionic surfactants such as polyoxyethylene/polyoxypropylene copolymers (commercially known as Pluronic®) have demonstrated equally good imaging capability when compared to that of the original formulations made with the pure substances taken alone. It is therefore, believed that the invention offers a more generalized concept of ultrasound media and offers better insight into the problems of ultrasound imaging as well as better control of contrast agent properties. The media and contrast agents containing the media of the invention are, therefore, considered as products which take the technique one step further in its development.

The invention also comprises a method of making the ultrasound contrast agent, in which a gas mixture of at least two components is suspended in a physiologically acceptable aqueous carrier liquid containing usual surfactants and stabilizers so as to form gas filled microbubbles or microballoons, characterized in that the minimum effective proportion of at least one gas component (B) in said mixture of gases is determined according to the criteria $$B_c \% = K/e^{bM_{wt}} + C$$

in which $B_c$ % (by vol.) is the total quantity of the component B in the mixture, K & C are constants with values of 140 and −10.8 respectively, $M_{wt}$ represents the molecular weight of the component B exceeding 80 and b is quantity that is a complex function of operating temperature and thickness of the membrane (a lipid film) that stabilizes the microbubbles; however, since the body temperature is substantially constant and the stabilizer film structure substantially independent of lipid concentration, the value of b keeps in the interval 0.011–0.012 and it may be considered as constant. The contrast agents made according to the method comprise suspensions of microbubbles or microballoons with excellent resistance to pressure variations and a relatively rapid resorption. Both of the properties are controlled to the extent that practically custom-tailored echographic agents are now possible. With the above criteria it is possible to produce an agent with desired characteristics starting from any available non-toxic ("off the shelf") substance which at body temperature is gas and which has the molecular weight and solubility in water as explained above.

The invention also includes a dry formulation comprising surfactants, additives and stabilizers stored under a mixture of substances which at the body temperature are gases at least one of which is a gas whose molecular weight is greater than 80 daltons and whose solubility in water is below 0.0283 ml per ml of water under standard conditions. Prior to injection the formulation comprising lyophilised film forming surfactants and optionally, hydrating agents like polyethylene glycol or other conventional hydrophilic substances, is admixed with a physiologically acceptable carrier liquid to produce the ultrasound contrast agent of the invention. The film forming surfactant is, preferably, a phospholipid selected from phosphatidic acid, phosphatidylcholine, phosphatidylethanolamine, phosphatidylserine, phosphatidylglycerol, phosphatidylinositol, cardiolipin, sphingomyelin and mixtures thereof.

In a variant, stabilization of the microbubble evanescent gas/liquid envelope may be secured by non-ionic surfactants such as copolymers of polyoxyethylene and polyoxypropylene in combination with a film forming surfactant such as dipalmitoylphosphatidylglycerol. As before the aqueous liquid carrier may further contain hydrophilic additives such as glycerol, PEG, sorbitol, etc. Furthermore, useful agents of the invention may be prepared with saline solutions containing Tween® 20 (Polyethylene Oxide Sorbitan ester), sorbitol, soybean oil, and optionally other additives.

Also disclosed is a two-component kit comprising as the first component a dry formulation of surfactants, additives and stabilizers stored under a mixture of gases and as the second component a physiologically acceptable carrier liquid which when brought in contact with the first component provides an ultrasound contrast media. The kit may include a system of two separate vials, each containing one of the components, which are interconnected so that the components may be conveniently brought together prior to use of the contrast agent. Clearly, the vial containing the dry formulation will at the same time contain the ultrasound medium of the invention. Conveniently, the kit may be in the form of a pre-filled two compartment syringe and may further include means for connecting a needle on one of its ends.

The invention further comprises a method of making contrast agents with microbubbles containing the ultrasound contrast media, as well as their use in imaging of organs in human or animal body.

When used for imaging of organs in human or animal body the ultrasound contrast medium of the invention is administered to the patient in the form of an aqueous suspension in the above described physiologically acceptable carrier liquid and the patient is scanned with an ultrasound probe whereby an image of the organ or the part of the body imaged is produced.

The invention described herein can be further elucidated by the description of the following representative (but not limiting) embodiments numbered 1–21:

1. An ultrasound contrast medium comprising substances gaseous at body temperature which when in suspension in an aqueous carrier liquid containing usual surfactants, additives and stabilizers provide agents for ultrasound echography, characterized in that the medium is a mixture of gases (A) and (B) at least one of which is a gas (B) whose molecular weight is greater than 80 daltons and whose solubility in water is below 0.283 ml of gas per ml of water at standard conditions.

2. The ultrasound contrast medium of embodiment 1, wherein proportion of gas B in the mixture is 0.5–41% by vol. and the proportion of gas A is 59–99.5% by vol.

3. The ultrasound contrast medium of embodiment 1 or 2, wherein the gas with molecular weight above 80 daltons is selected from the group consisting of $SF_6$, $CF_4$, $C_2F_6$, $C_2F_8$, $C_3F_6$, $C_3F_8$, $C_4F_6$, $C_4F_8$, $C_4F_{10}$, $C_5F_{10}$, $C_5F_{12}$ and mixtures thereof.

4. The ultrasound contrast medium of embodiment 3, wherein the gas B is sulfur hexafluoride or octafluorocyclobutane.

5. The ultrasound contrast medium of embodiment 1 or 2, wherein the gas A is selected from the group consisting of air, oxygen, nitrogen, carbon dioxide and mixtures thereof.

6. An ultrasound contrast agent consisting of a suspension of gas filled microbubbles or microballoons in a physiologically acceptable aqueous carrier comprising usual surfactants, additives and stabilizers, characterized in that the gas is a mixture of at least two gases A and B in which at least one gas (B) has a molecular weight greater than 80 daltons and solubility in water is below 0.0283 ml per ml of water at standard conditions.

7. The ultrasound contrast agent of embodiment 6, wherein the mixture contains 0.5–41% by vol. of gas B and 59–99.5% by vol. of gas A.

8. The ultrasound contrast agent of embodiment 6 or 7, wherein the gas B with molecular weight above 80 daltons is selected from the group consisting of $SF_6$, $CF_4$, $C_2F_6$, $C_2F_8$, $C_3F_6$, $C_3F_8$, $C_4F_6$, $C_4F_8$, $C_4F_{10}$, $C_5F_{10}$, $C_5F_{12}$ and mixtures thereof.

9. The ultrasound contrast agent of embodiment 7, wherein the gas A is selected from the group consisting of air, oxygen, nitrogen, carbon dioxide or mixtures thereof.

10. The ultrasound contrast agent of embodiment 7, wherein the surfactants comprise at least one film forming surfactant present in laminar and/or lamellar form and, optionally, hydrophilic stabilizers.

11. The ultrasound contrast agent of embodiment 7, wherein the film forming surfactant is a phospholipid.

12. The ultrasound contrast agent of embodiment 7, wherein the phospholipid is selected from the group consisting of phosphatidic acid, phosphatidylcholine, phosphatidylethanolamine, phosphatidylserine, phosphatidylglycerol, phosphatidylinositol, cardiolipin, sphingomyelin, and mixtures therein.

13. The ultrasound contrast agent of embodiment 11, wherein in addition to the phospholipid the aqueous carrier comprises copolymers of polyoxyethylene and polyoxypropylene, and glycerol.

14. The ultrasound contrast agent of embodiment 7, wherein the surfactants, additives and stabilizers comprise soy bean oil and Tween® and sorbitol.

15. A dry formulation comprising surfactants, additives and stabilizers stored under a mixture of substances which at body temperature are gases at least one of which is a gas whose molecular weight is greater than 80 daltons and whose solubility in water is below 0.0283 ml per ml of water at standard conditions.

16. A two component kit comprising as the first component a dry formulation of surfactants, additives and stabilizers stored under a mixture of gases and as the second component a physiologically acceptable carrier liquid which when admixed with the first component provides, as a suspension of the two components, an ultrasound contrast medium, characterized in that at least one of the gases in the mixture is a gas whose molecular weight is greater than 80 daltons and whose solubility in water is below 0.028 ml of gas per ml of water at standard conditions.

17. A method of making the ultrasound contrast agent of embodiment 7, in which a gas mixture of at least two components (A and B) is suspended in a physiologically acceptable aqueous carrier liquid containing usual surfactants, additives and stabilizers so as to form, gas filled microbubbles or microballoons, characterized in that the minimum effective proportion of at least one gas component in said mixture of gases is determined according to the criteria $$B_c \% = K/e^{bM_{wt}} + C$$

in which $B_c$ % (by vol.) is the total quantity of the component B in the mixture, K, C and b are constants with values of 140, −10.8 and 0.012 respectively, $M_{wt}$ represents the molecular weight of the component B which is >80.

18. The method of making the ultrasound contrast agent of embodiment 17, wherein the surfactant is a phospholipid selected from the group consisting of phosphatidic acid, phosphatidyl-choline, phosphatidylethanolamine, phosphatidylserine, phosphatidyl-glycerol, phosphatidylinositol, cardiolipin, sphingomyelin and mixtures thereof.

19. Use of the ultrasound contrast medium of embodiment 1 for the: manufacture of contrast agents useful in imaging the cardiovascular systems of humans or animals.

20. Use of the ultrasound contrast medium of embodiment 1 for the manufacture of ultrasound contrast agents.

21. Use of the ultrasound contrast agent of embodiment 1 for imaging of human or animal body.

The following examples further illustrate the invention:

EXAMPLE 20

Multilamellar vesicles (MLVs) were prepared by dissolving 120 mg of diarachidoylphosphatidylcholine (DAPC, from Avanti Polar Lipids) and 5 mg of dipalmitoylphosphatidic acid (DPPA acid form, from Avanti Polar Lipids) in 25 ml of hexane/ethanol (8/2, v/v) then evaporating the solvents to dryness in a round-bottomed flask using a rotary evaporator. The residual lipid film was dried in a vacuum desiccator and after addition of water (5 ml), the mixture was incubated at 90° C. for 30 minutes under agitation. The resulting solution was extruded at 85° C. through a 0.8 μm polycarbonate filter (Nuclepore®). This preparation was added to 45 ml of a 167 mg/ml solution of dextran 10,000 MW (Fluka) in water. The solution was thoroughly mixed, transferred in a 500 ml round-bottom flask, frozen at −45° C. and lyophilised under 13.33 Nt/m² (0.1 Torr). Complete sublimation of the ice was obtained overnight. Aliquots (100 mg) of the resulting lyophilisate were introduced in 20 ml glass vials. The vials were closed with rubber stoppers and the air removed from vials using vacuum. Mixtures of air with various amounts of sulfur hexafluoride were introduced into the vials via a needle through the stopper.

Bubble suspensions were obtained by injecting in each vial 10 ml of a 3% glycerol solution in water followed by vigorous mixing. The resulting microbubble suspensions were counted using a hemacytometer. The mean bubble size was 2.0 μm. In vitro measurements (as defined in EP-A-0 554 213) of the critical pressure (Pc), echogenicity (i.e., backscatter coefficient) and the bubble count for various samples were performed (see Table 9).

TABLE 9

| Sample | air % vol | $SF_6$ % vol | Q coeff. | PC mmHg | Echogenicity 1/(cm.sr) × 100 | Concentration (bubbles/ml) |
|---|---|---|---|---|---|---|
| A | 100 | 0 | 1.0 | 43 | 1.6 | $1.5 \times 10^8$ |
| B | 95 | 5 | 1.3 | 68 | 2.1 | $1.4 \times 10^8$ |
| C | 90 | 10 | 1.6 | 85 | 2.4 | $1.5 \times 10^8$ |
| D | 75 | 25 | 3.1 | 101 | 2.3 | $1.4 \times 10^8$ |
| E | 65 | 35 | 4.7 | 106 | 2.4 | $1.5 \times 10^8$ |
| F | 59 | 41 | 5.8 | 108 | 2.4 | $1.6 \times 10^8$ |
| G | 0 | 100 | 722.3 | 115 | 2.3 | $1.5 \times 10^8$ |

As it may be seen from the results, the microbubbles containing 100% air (sample A) have a low resistance to pressure. However, with only 5% $SF_6$, the resistance to pressure increases considerably (sample B). With 25% $SF_6$ the resistance to pressure is almost identical to that of 100% $SF_6$. On the other hand, the bubble concentrations, the mean bubble sizes and the backscatter coefficients are almost independent of the percentage of $SF_6$.

The resulting suspensions were injected intravenously into minipigs (Pitman Moore) at a dose of 0.5 ml per 10 kg and the images of the left ventricular cavity were recorded on a video recorder. In vivo echographic measurements were performed using an Acuson XP128 ultrasound system (Acuson Corp. USA) and a 7 MHz sector transducer. The intensity of the contrast was measured by video densitometry using an image analyzer (Dextra Inc.). FIG. 6 shows the video densitometric recordings in the left heart of a minipig. Again a considerable difference is observed between the 100% air case (sample A) and the 95% air case (sample B). In particular, with 5% $SF_6$ the maximum intensity is already almost achieved and the half life in circulation shows also a very rapid increase. With 10% $SF_6$, there is no additional increase in intensity but only a prolongation of the half-life. From the example, it follows that using more than 10% to 25% $SF_6$ in the gas mixture provides no real benefit. It is interesting to note that the values of the Q coefficient obtained for the mixtures used were well below the critical value of 5 stipulated by WO-A-93/05819.

EXAMPLE 21

Aliquots (25 mg) of the PEG/DAPC/DPPA lyophilisate obtained as described in Example 20 (using PEG 4000 instead of dextran 10,000) were introduced in 10 ml glass vials. Tedlar® sampling bags were filled with air and octafluorocyclobutane ($C_4F_8$). Known volumes were withdrawn from the bags by syringes and the contents thereof were mixed via a three way stopcock system. Selected gas mixtures were then introduced into the glass vials (previously evacuated). The lyophilisates were then suspended in 2.5 ml saline (0.9% NaCl). The results presented below show the resistance to pressure, the bubble concentration and the backscanter coefficient of the suspensions. In the case of 100% $C_4F_8$ the resistance to pressure reached to 225 mm Hg (compared to 43 mm Hg in the case of air). Again a considerable increase in pressure resistance was already observed with only 5% $C_4F_8$ (Pc=117 mmHg).

After intra-aortic injection in rabbits (0.03 ml/kg), a slight prolongation of the contrast effect in the myocardium was noticed already with 2% $C_4F_8$ (when compared to air). However with 5% $C_4F_8$, the duration of the contrast increased considerably as if above a threshold value in the resistance to pressure, the persistence of the bubbles increases tremendously (see FIG. 7).

TABLE 10

| Sample | air % vol | $C_4F_8$ % vol | Q coeff. | PC mmHg | Echogenicity 1/(cm.sr) × 100 | Concentration (bubbles/ml) |
|---|---|---|---|---|---|---|
| A | 100 | 0 | 1.0 | 43 | 1.6 | $1.8 \times 10^8$ |
| B | 95 | 5 | 1.4 | 117 | 2.2 | $3.1 \times 10^8$ |
| C | 90 | 10 | 1.7 | 152 | 3.1 | $4.7 \times 10^8$ |
| D | 75 | 25 | 3.3 | 197 | 3.5 | $4.9 \times 10^8$ |
| E | 65 | 35 | 4.6 | 209 | 3.4 | $4.3 \times 10^8$ |
| F | 59 | 41 | 5.5 | 218 | 2.8 | $4.0 \times 10^8$ |
| G | 0 | 100 | 1531 | 225 | 2.3 | $3.8 \times 10^8$ |

Here again, this combination of gases provided very good images at 5% of gas B in the mixture, while excellent images of the left heart were obtained with the mixtures containing up to 25% of octafluorocyclobutane. Corresponding diagram of critical pressure as a function of $C_4F_8$ in the mixture with air is given in FIG. 3. This example again shows that the use of mixture of gases allows to improve considerably the resistance to pressure of air bubbles simply by adding a small percentage of a high molecular weight/low solubility gas. The figure further shows that by appropriate selection of the gas mixture it becomes possible to obtain any desired resistance to pressure.

EXAMPLE 22

The same lyophilisate as that described in Example 24 was used. The gas phase was made of dodecafluoropentane ($C_5F_{12}$) and air. $C_5F_{12}$ is a liquid at room temperature with a boiling point of 29.5° C. 24 ml glass vials each containing 50 mg of the PEG/DSPC/DPPG lyophilisate obtained as described in Example 24 were put under vacuum, closed under vacuum, then heated at 45° C. Small volumes (a few microliters) of $C_5F_{12}$ were injected in the vials still at 45° C. through the stopper. Air was then introduced to restore atmospheric pressure in the vials. After cooling at room temperature, saline (5 ml) was injected through the stopper and the vials were vigorously agitated. The actual percentage of $C_5F_{12}$ in the gas phase was calculated assuming full vaporization of the liquid introduced. This is an overestimate as at this temperature part of the liquid will not be in gaseous state. As shown in FIG. 4 an increase in the resistance to pressure could already be detected with only 0.5% $C_5F_{12}$ in air. At 1.4% $C_5F_{12}$ the resistance to pressure exceeded 130 mm Hg. These suspensions were also injected intravenously into minipigs (0.5 ml per 15 kg). Intensity was measured by videodensitometry as described in Example 20. As shown in Table 11, maximum intensity was already obtained with 1.4% $C_5F_{12}$. Higher percentages of $C_5F_{12}$ result into prolongation of the half life and increase in the AUC. The half life ($t_{1/2}$) was determined as the time elapsed between injection and the time at which the intensity had dropped to 50% of its maximum value. The area under the curve (AUC) was measured until $t_{1/2}$.

The Examples 20–22 also demonstrate that contrary to the statements made in WO-A-93/05819 it is possible to obtain outstanding contrast enhancing agents from gas mixtures whose Q values are smaller and in certain cases much smaller than 5.

EXAMPLE 23

Fifty eight milligrams of diarachidoylphosphatidylcholine (DAPC), 2.4 mg of dipalmitoylphosphatidic acid (DPPA) both from Avanti Polar Lipids (USA) and 3.94 g of polyethyleneglycol (PEG 4000 from Siegfried) were dissolved at 60° C. in tert-butanol (20 ml) in a round-bottom glass vessel. The clear solution was rapidly cooled at −45° C. and lyophilized. Aliquots (25 mg) of the white cake obtained were introduced in 10 ml glass vials.

Tedlar® gas sampling bags were filled with gases, one with air and one with sulfur hexafluoride ($SF_6$). Predetermined volumes of the gases were collected from each bag through the septum by using two separate syringes and the contents mixed via a three way stopcock. The resulting gas mixtures were introduced into 10 ml glass vials which were evacuated and closed with rubber stopper while still under vacuum. Seven vials contained gas mixtures of air and $SF_6$ in different proportions. The concentration of $SF_6$ was between 0 to 100%. The actual percentage of $SF_6$ in the gas phase was confirmed by densitometry (A. Paar densimeter). Saline (0.9% NaCl) was then injected through the stopper into each vial (5 ml per vial) and the powder dissolved by vigorous shaking. The resulting microbubble suspensions were evaluated in vitro and in vivo. The resistance to

TABLE 11

| Sample | air % vol | $C_5F_{12}$ % vol | Q coeff. | Pc mmHg | Echogen (cm.sr)$^{-1}$ | Conc. (bub/ml) | half-life ($t_{1/2}$) sec | Inten Gray level | AUC ($t_{1/2}$) |
|---|---|---|---|---|---|---|---|---|---|
| A | 100 | 0 | 1 0 | 43 | 0.017 | $1.8 \times 10^8$ | 11 | 22 | 78 |
| B | 99.5 | 0.5 | 1.0 | 80 | — | — | — | — | — |
| C | 98.6 | 1.4 | 1.1 | 133 | 0.026 | $3.9 \times 10^8$ | 14 | 97 | 609 |
| D | 97.1 | 2.9 | 1.4 | 182 | 0.028 | $3.9 \times 10^8$ | 17 | 98 | 860 |
| E | 94.2 | 5.8 | 1.7 | 295 | 0.040 | $5.2 \times 10^8$ | 59 | 99 | 3682 |
| F | 85.5 | 4.5 | 3.4 | 394 | 0.036 | $4.5 \times 10^8$ | 78 | 97 | 5141 |

*Estimated pressure $P_c$ was determined using a nephelometric assay and the backscatter coefficient was measured using a pulse echo set up (both described in EP-A-0 554 213). The bubble concentration and mean bubble size were determined by analysis with a Coulter Multisizer II (Coulter Electronics Ltd). The results obtained were virtually the same to those given for Example 20.

TABLE 12

| Gas A | Gas B | Gas B % vol | Pc mmHg | Gas A $M_{wt}$ | Gas B $M_{wt}$ | Solubility* Gas A | Solubility* Gas B |
|---|---|---|---|---|---|---|---|
| $O_2$ | $C_4F_8$ | 0 | 40 | 32 | 200 | 0.083 | 0.016 |
|  | $C_4F_8$ | 5 | 112 |  |  |  |  |
|  | $C_4F_8$ | 10 | 148 |  |  |  |  |
| $CO_2$ | $C_4F_8$ | 0 | 50 | 44 | 200 | 0.74 | 0.016 |
|  | $C_4F_8$ | 5 | — |  |  |  |  |
|  | $C_4F_8$ | 10 | 204 |  |  |  |  |
| $CHClF_2$ | $C_4F_8$ | 0 | — | 86.5 | 200 | 0.78 | 0.016 |
|  | $C_4F_8$ | 5 | 106 |  |  |  |  |
|  | $C_4F_8$ | 10 | 163 |  |  |  |  |
| Xenon | $C_4F_8$ | 0 | 50 | 131 | 200 | 0.108 | 0.016 |
|  | $C_4F_8$ | 5 | 147 |  |  |  |  |
|  | $C_4F_8$ | 10 | 181 |  |  |  |  |
| $SF_6$ | $C_4F_8$ | 0 | 124 | 146 | 200 | 0.005 | 0.016 |
|  | $C_4F_8$ | 5 | 159 |  |  |  |  |
|  | $C_4F_8$ | 10 | 193 |  |  |  |  |
| $N_2$ | $SF_6$ | 0 | 55 | 28 | 146 | 0.0144 | 0.005 |
|  | $SF_6$ | 5 | 80 |  |  |  |  |
|  | $SF_6$ | 10 | 108 |  |  |  |  |
| $CF_4$ | $SF_6$ | 0 | 84 | 182 | 146 | 0.0038 | 0.005 |
|  | $SF_6$ | 5 | 91 |  |  |  |  |
|  | $SF_6$ | 10 | 106 |  |  |  |  |
| Xenon | $SF_6$ | 0 | 50 | 131 | 146 | 0.108 | 0.005 |
|  | $SF_6$ | 5 | 67 |  |  |  |  |
|  | $SF_6$ | 10 | 83 |  |  |  |  |

*Bunsen coefficient

EXAMPLE 24

A PEG/DSPC/DPPG lyophilisate was prepared as described in Example 23 using 30 mg of distearoylphosphatidylcholine (DSPC) and 30 mg dipalmitoylphosphatidylglycerol (DPPG) (both from SYGENA, Switzerland). Aliquots (25 mg) of the resulting cake were introduced in 10 ml glass vials. Different gas mixtures were introduced in various vials by withdrawing appropriate volumes from Tedlar® bags filled with the various gases. Table 12 shows the gas mixtures investigated, their molecular weight and their solubilities (expressed as Bunsen coefficient) and the resistance to pressure of the microbubbles obtained. It is particularly interesting to note that highly soluble gases such as $CO_2$, xenon, $CHClF_2$ which alone are very poor in their ability to form stable and resistant bubbles are nevertheless able to give rise to highly stable bubbles provided a small percentage of a gas such as $SF_6$ or $C_4F_8$ is added.

EXAMPLE 25

The method of the invention was applied to a microbubble suspension prepared as described in Example 1 of WO 92/11873. Three grams of Pluronic® F68 (a copolymer of polyoxyethylene-polyoxypropylene with a

TABLE 13

|  |  | Pc | right ventr. opacif. | | | left ventr. opacif. | | |
|---|---|---|---|---|---|---|---|---|
| air % vol | $C_4F_8$ % vol | (mmHg) | $t_{1/2}$ | intens | AUC | $t_{1/2}$ | intens | AUC |
| 100 | 0 | 54 | 4 | 96 | 280 | 9 | 101 | 514 |
| 99 | 1 | 89 | 7 | 98 | 377 | 12 | 98 | 632 |

TABLE 13-continued

|  |  | Pc | right ventr. opacif. | | | left ventr. opacif. | | |
|---|---|---|---|---|---|---|---|---|
|  |  | (mmHg) | $t_{1/2}$ | intens | AUC | $t_{1/2}$ | intens | AUC |
| 95 air | 5 $C_5F_{12}$ | 136 | 14 | 94 | 829 | 40 | 101 | 2693 |
| 95 | 5 | 177 | * | * | * | 43 | 111 | 3249 |

*Shadowing molecular weight of 8400), 1 g of dipalmitoylphosphatidylglycerol and 3.6 g of glycerol were added to 80 ml of distilled water. After heating at about 80° C. a clear homogenous solution was obtained. The tenside solution was cooled to room temperature and the volume adjusted to 100 ml. The bubble suspension was obtained by using two syringes connected via a three-way valve. One of the syringes was filled with 5 ml of the tenside solution while the other was filled with 0.5 ml of air or air/$C_4F_8$ mixture (see Table 13). The three way valve was filled with the tenside solution before it was connected to the gas-containing syringe. By alternatively operating the two pistons, the tenside solution was transferred back and forth between the two syringes (5 times in each direction) and milky suspensions were obtained. After dilution (1/50) in distilled water saturated with air the resistance to pressure (Pc) was determined. Aliquots were injected intravenously into anaesthetized rabbits (0.03 ml/kg) and echographic images of the left ventricle were recorded. The area under the curve (AUC) as well as the half life ($t_{1/2}$) were determined. A considerable increase of the half-life and AUC was observed when using 5% $C_4F_8$ (compared to air). Similar results were obtained with 5% $C_5F_{12}$.

EXAMPLE 26

A suspension of microbubbles was obtained as described in WO-A-93/05819 using mixtures of air and octafluorocyclobutane $C_4F_8$. An aqueous solution containing sorbitol (20 g), NaCl (0.9 g), soybean oil (6 ml), Tween 20

TABLE 14

| air % vol | $C_4F_8$ % vol | right ventr. opacif | left ventr. opacif. | air % vol | $C_5F_{12}$ % vol | right ventr. opacif. | left ventr. opacif. |
|---|---|---|---|---|---|---|---|
| 100 | 0 | + | − | 100 | 0 | + | − |
| 99 | 1 | + | − | 99 | 1 | + | + |
| 95 | 5 | ++ | − | 95 | 5 | ++ | ++ |

− no opacification
+ moderate opacification
++ good opacification (0.5 ml) was prepared and adjusted to 100 ml of distilled water. 10 ml of this solution was taken up in a 10 ml syringe. A second 10 ml syringe was filled with mixtures of air and $C_4F_8$. The two syringes were connected via a three way stopcock. By operating alternatively each of the two pistons for a total of 20 times, milky suspensions were obtained. These suspensions were tested for their resistance to pressure. Aliquots were also injected intravenously into anaesthetized rabbits (0.1 ml/kg) and echographic images of the left ventricle were recorded. Interestingly no contrast was detected in the left ventricle with 1% or even 5% $C_4F_8$. However, left ventricle opacification was obtained with 1% and even more with 5% of $C_5F_{12}$.

EXAMPLE 27

A PEG/DSPC/DPPG lyophilisate was prepared as described in Example 23 using 30 mg of distearoylphosphatidylcholine (DSPC) and 30 mg dipalmitoylphosphatidylglycerol (DPPG) (both from SYGENA, Switzerland). Aliquots (25 mg) of the resulting cake were introduced in 10 ml glass vials. Different gas mixtures were introduced in various vials by withdrawing appropriate volumes from Tedlar® bags filled with the various gases. Table 15 shows the gas mixtures investigated and the resistance to pressure of the microbubbles obtained. It is noteworthy the high molecular weight gas may even be a mixture of two or more gases with high molecular weight and

TABLE 15

| Sample | $C_4F_8$ % vol | $CF_4$ % vol | Air % vol | Pc mmHg | Absorbance |
|---|---|---|---|---|---|
| A1 | 5 | 15 | 80 | 113 | 0.284 |
| A2 | 10 | 10 | 80 | 147 | 0.281 |
| A3 | 15 | 5 | 80 | 167 | 0.281 | solubility (expressed as Bunsen coefficient) which is below 0.0283. It follows that in place of a single gas (B), mixtures of two or more activating or minor component gases may also be used. Although, in this example, the critical pressure is proportional to the percentage of the heavier of the two components, it is believed that other combinations of gases may further lower the total amount of the insoluble gas(es) in the mixture through synergy.

We claim:

1. An ultrasound contrast agent comprising an aqueous solution and phospholipid stabilized microbubbles, the phospholipid stabilized microbubbles containing gas comprising a freon wherein the gas is stabilized by phospholipids in lamellar or laminar form at the gas/liquid interface.

2. The ultrasound contrast agent of claim 1 wherein the gas further comprises nitrogen.

3. The ultrasound contrast agent of claim 1, wherein the phospholipids comprise saturated synthetic lecithin.

4. The ultrasound contrast agent of claim 1, wherein the phospholipids comprise dipalmitoylphosphatidylcholine.

5. The ultrasound contrast agent of claim 1, wherein the phospholipids comprise dipalmitoylphosphatidic acid.

* * * * *